(12) United States Patent
Cleek et al.

(10) Patent No.: US 10,039,863 B2
(45) Date of Patent: Aug. 7, 2018

(54) DRUG ELUTING COMPOSITE

(71) Applicant: W. L. Gore & Associates, Inc., Newark, DE (US)

(72) Inventors: Robert L. Cleek, Flagstaff, AZ (US); Edward H. Cully, Flagstaff, AZ (US); Jeffrey B. Duncan, Flagstaff, AZ (US); Theresa A. Holland, Flagstaff, AZ (US); Thomas R. McDaniel, Flagstaff, AZ (US); Christine M. Scotti, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 15/362,008

(22) Filed: Nov. 28, 2016

(65) Prior Publication Data

US 2017/0072115 A1 Mar. 16, 2017

Related U.S. Application Data

(63) Continuation of application No. 13/103,885, filed on May 9, 2011, now Pat. No. 9,504,771, which is a continuation-in-part of application No. 12/941,839, filed on Nov. 8, 2010, now Pat. No. 9,320,890, which is a continuation-in-part of application No. 12/909,609, filed on Oct. 21, 2010.

(60) Provisional application No. 61/259,491, filed on Nov. 9, 2009.

(51) Int. Cl.
| | | |
|---|---|---|
| *A61L 31/10* | (2006.01) | |
| *A61L 29/16* | (2006.01) | |
| *A61L 29/08* | (2006.01) | |
| *A61L 31/16* | (2006.01) | |
| *A61N 1/05* | (2006.01) | |

(52) U.S. Cl.
CPC ............. *A61L 31/10* (2013.01); *A61L 29/085* (2013.01); *A61L 29/16* (2013.01); *A61L 31/16* (2013.01); *A61L 2300/222* (2013.01); *A61L 2300/608* (2013.01); *A61L 2420/08* (2013.01); *A61N 1/056* (2013.01); *A61N 1/0568* (2013.01)

(58) Field of Classification Search
None
See application file for complete search history.

(56) References Cited

U.S. PATENT DOCUMENTS

| | | | |
|---|---|---|---|
| 3,892,238 | A | 7/1975 | Banford et al. |
| 3,926,188 | A | 12/1975 | Baker et al. |
| 4,596,555 | A | 6/1986 | Theeuwes |
| 4,601,893 | A | 7/1986 | Cardinal |
| 5,290,271 | A | 3/1994 | Jernberg |
| 5,578,069 | A | 11/1996 | Miner, II |
| 5,605,696 | A | 2/1997 | Eury et al. |
| 5,662,698 | A | 9/1997 | Altman et al. |
| 6,306,428 | B1 | 10/2001 | Lehmann et al. |
| 6,753,071 | B1 | 6/2004 | Pacetti |
| 7,014,913 | B2 | 3/2006 | Pacetti |
| 7,691,401 | B2 | 4/2010 | Castro et al. |
| 7,771,413 | B2 | 8/2010 | Massengale et al. |
| 2002/0138123 | A1 | 9/2002 | Casas-Bejar et al. |
| 2004/0024448 | A1 | 2/2004 | Chang et al. |
| 2005/0008673 | A1 | 1/2005 | Snyder et al. |
| 2005/0107738 | A1 | 5/2005 | Slater et al. |
| 2005/0113903 | A1 | 5/2005 | Rosenthal et al. |
| 2005/0208098 | A1 | 9/2005 | Castro et al. |
| 2006/0111626 | A1 | 5/2006 | Rossing et al. |
| 2006/0269475 | A1 | 11/2006 | Ryu et al. |
| 2006/0276885 | A1 | 12/2006 | Lye et al. |
| 2007/0299491 | A1 | 12/2007 | Borgaonkar et al. |
| 2008/0026034 | A1 | 1/2008 | Cook et al. |
| 2008/0075833 | A1 | 3/2008 | Pacetti |
| 2009/0087380 | A1 | 4/2009 | Fasching et al. |
| 2009/0132031 | A1 | 5/2009 | Cook et al. |
| 2009/0324676 | A1 | 12/2009 | Hofmann et al. |
| 2011/0066108 | A1 | 3/2011 | Geipel et al. |

FOREIGN PATENT DOCUMENTS

| | | |
|---|---|---|
| EP | 1545642 A1 | 6/2005 |
| EP | 1847290 A1 | 10/2007 |
| GB | 2440679 B | 12/2008 |
| JP | 4-224513 A | 8/1992 |
| WO | WO-00/25854 A2 | 5/2000 |

*Primary Examiner* — Robert A Wax
*Assistant Examiner* — Randeep Singh
(74) *Attorney, Agent, or Firm* — Kilpatrick Townsend & Stockton, LLP

(57) ABSTRACT

The present invention relates to materials having therapeutic compositions releasably contained within the materials. The materials are configured to release therapeutic compositions at a desired rate. The present invention also relates to devices incorporating the materials.

17 Claims, 40 Drawing Sheets

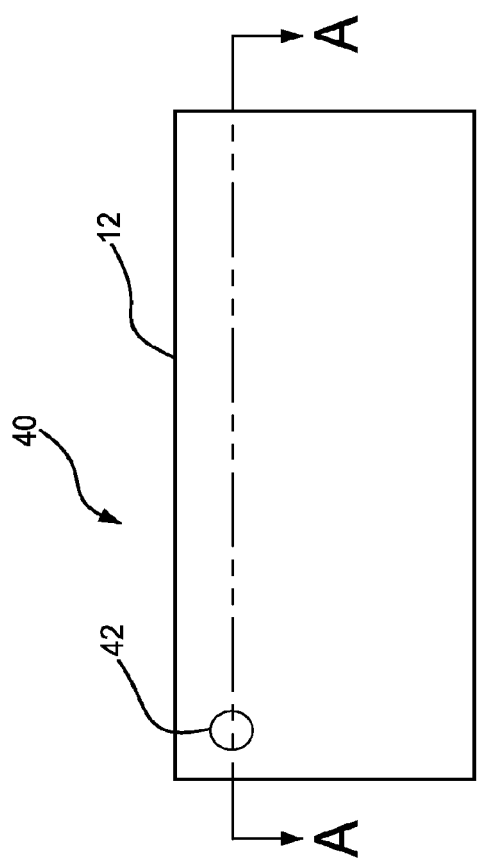
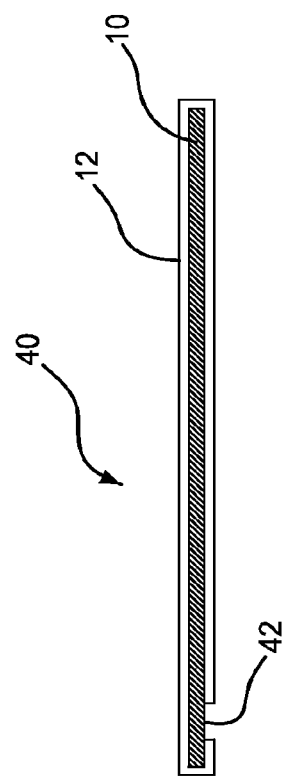
FIG. 8A
FIG. 8B

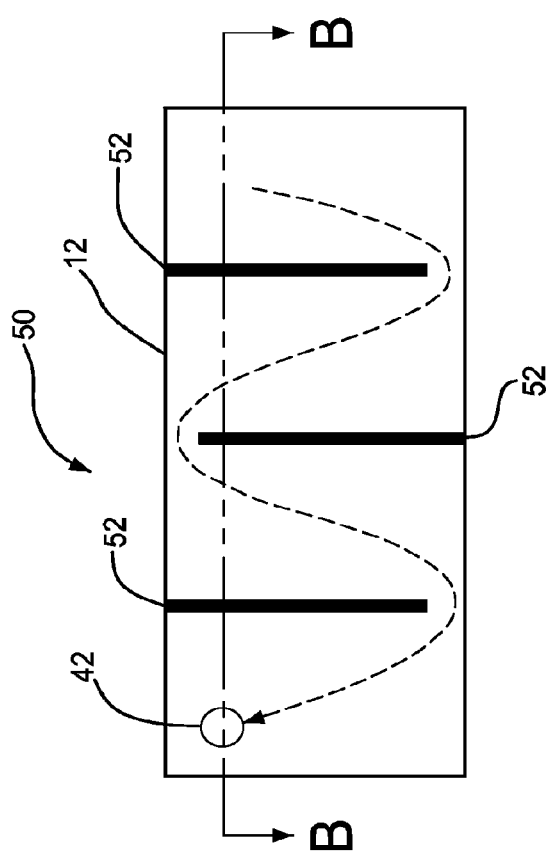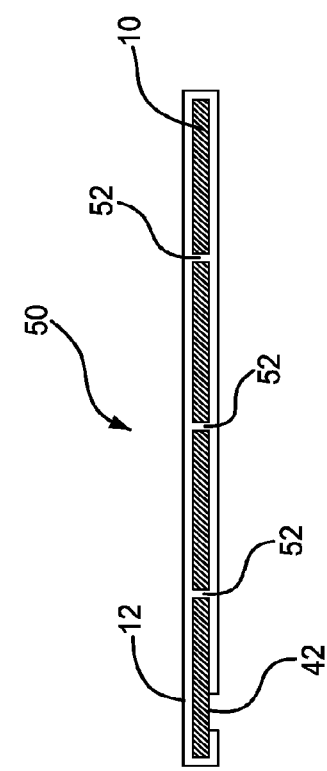

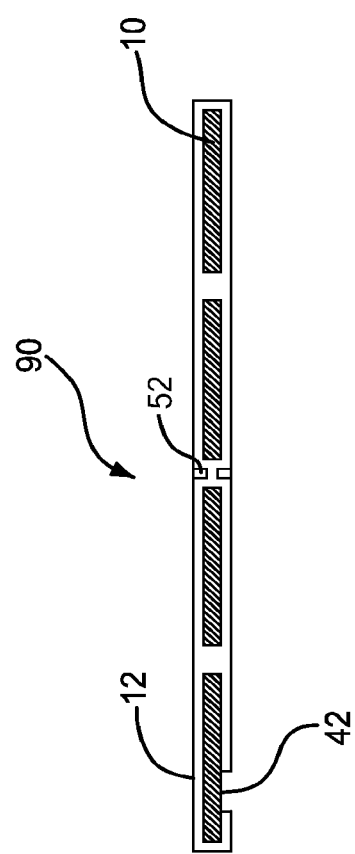

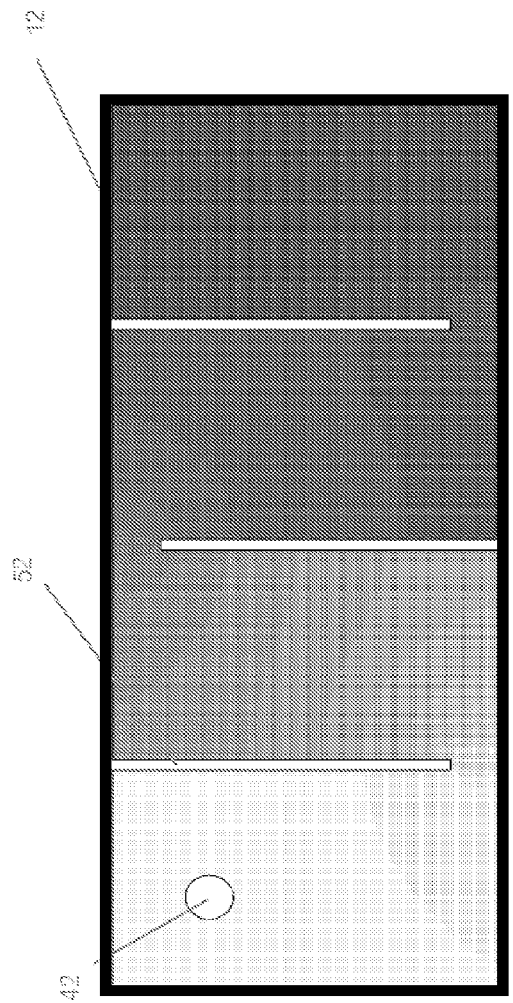
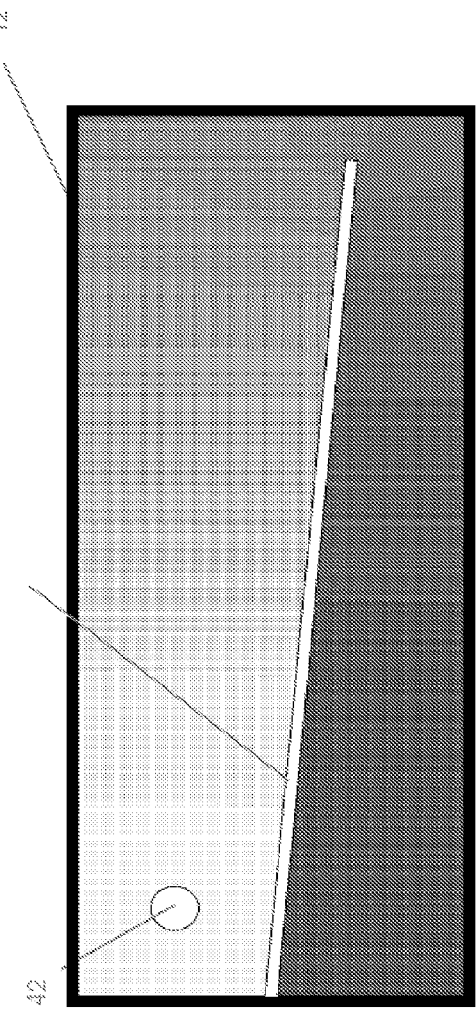
Fig. 22A
Fig. 22B

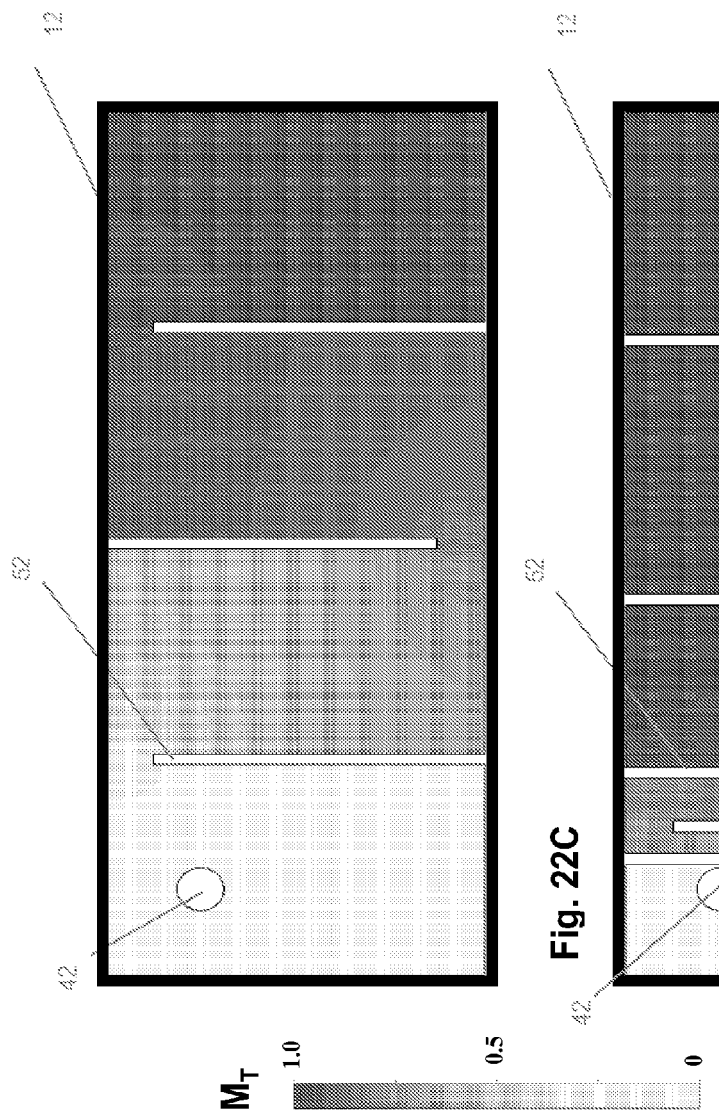

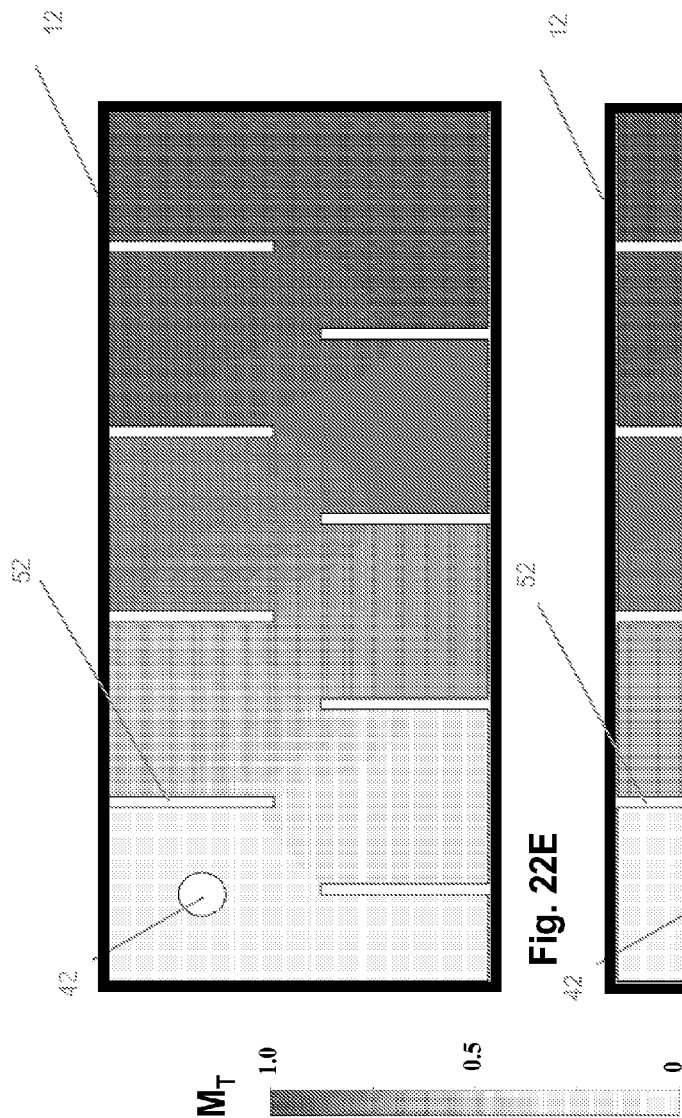
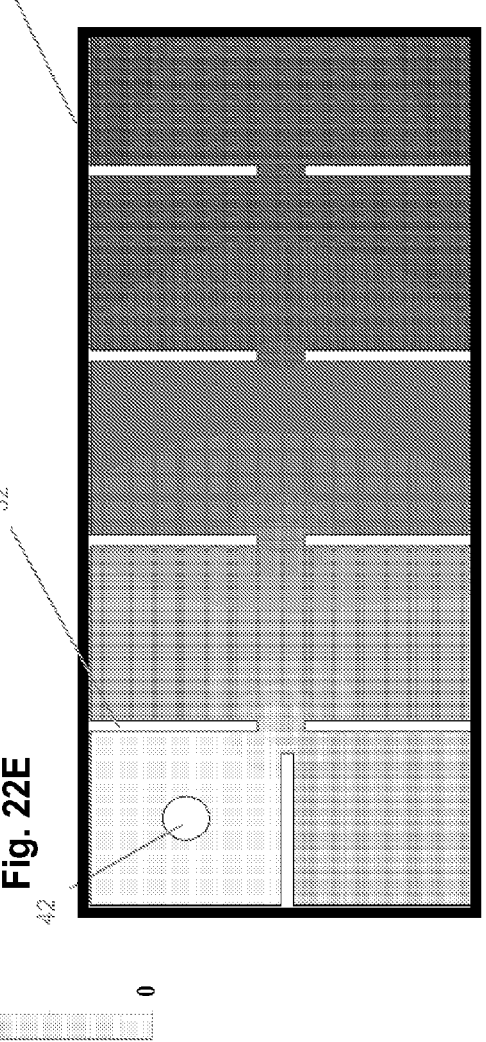
Fig. 22E
Fig. 22F

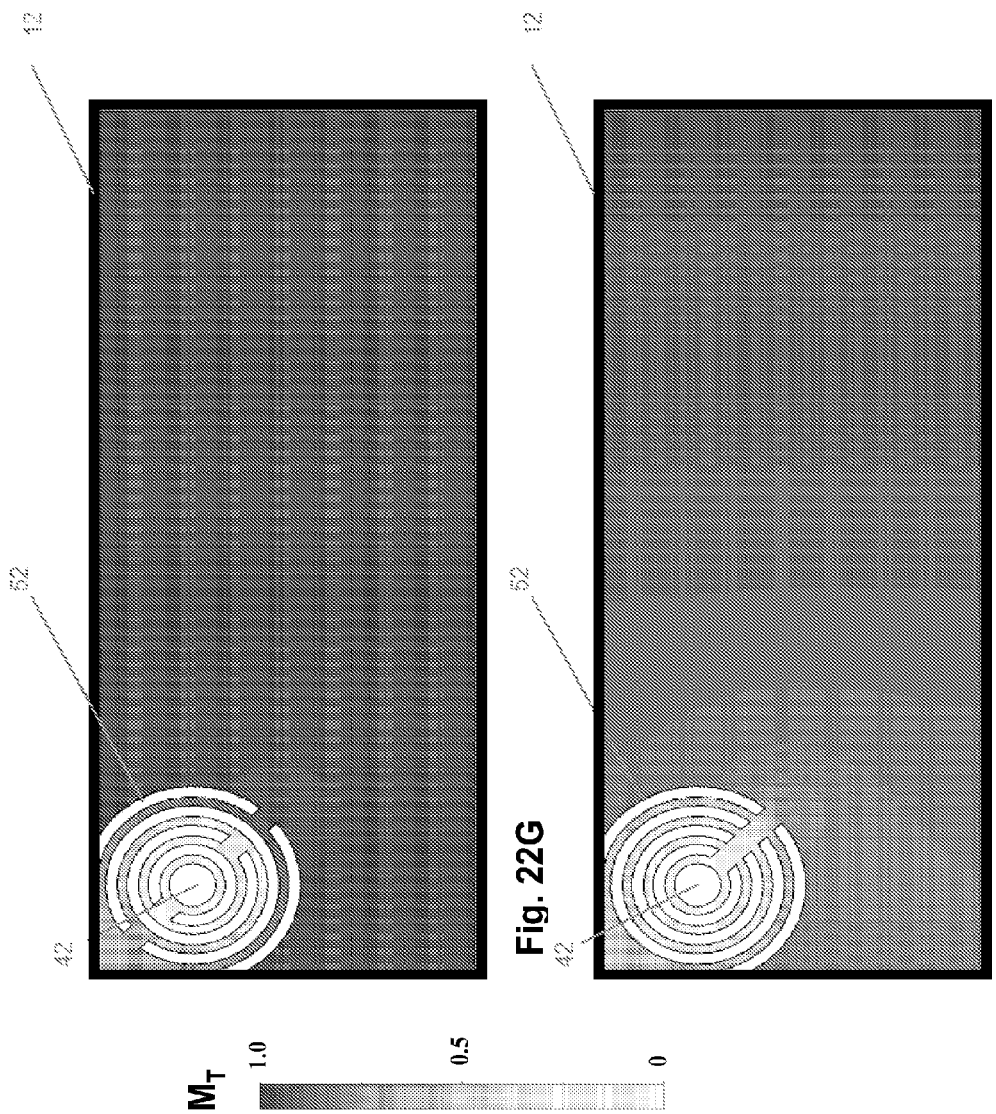

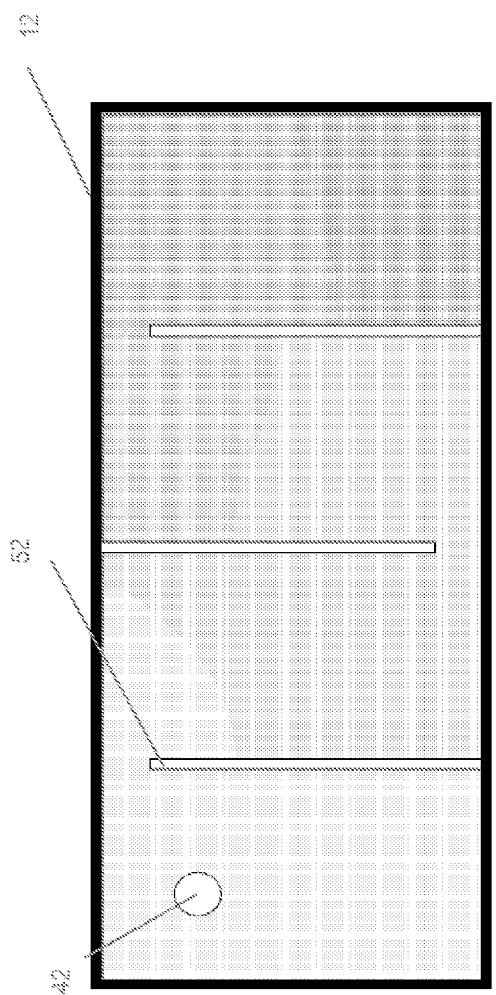
Fig. 23C
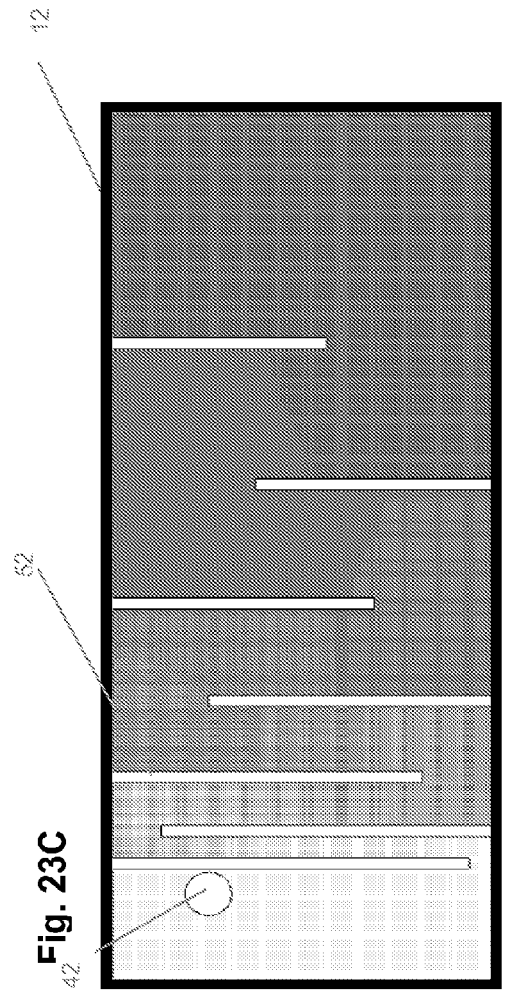
Fig. 23D

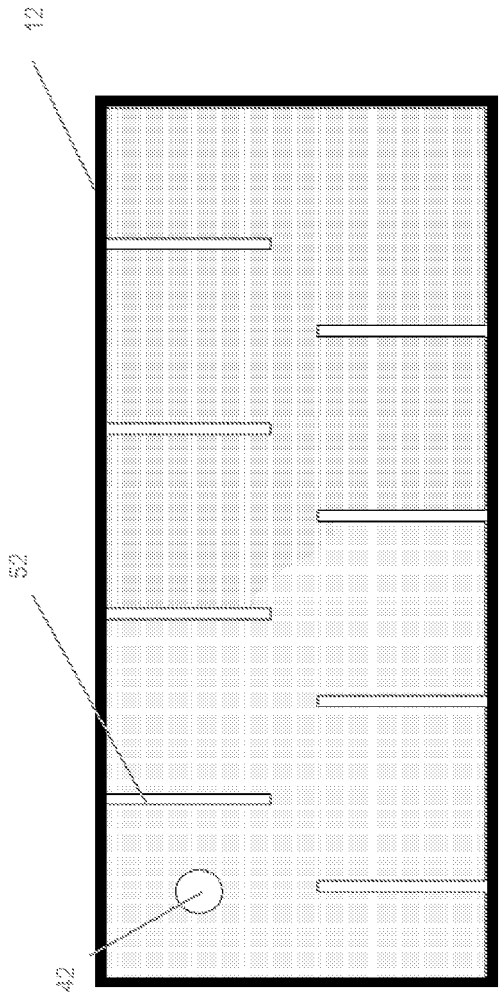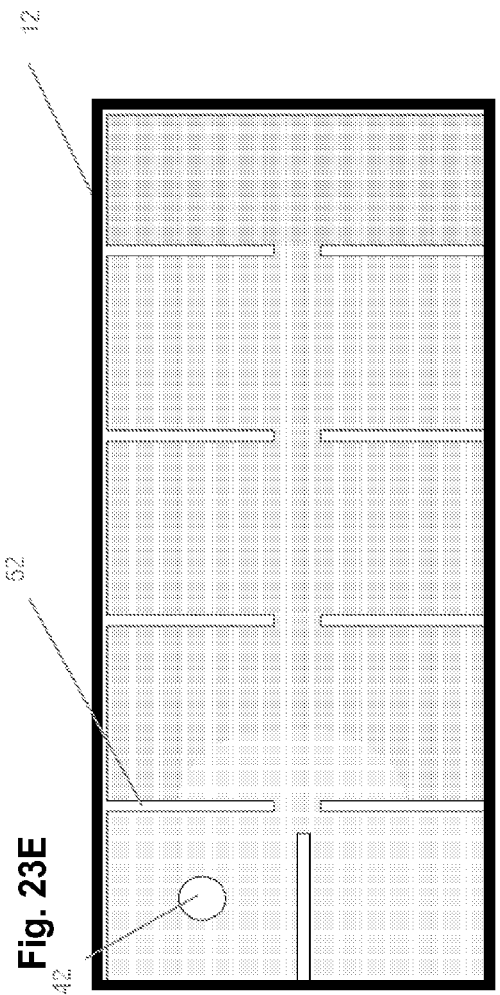
Fig. 23E
Fig. 23F

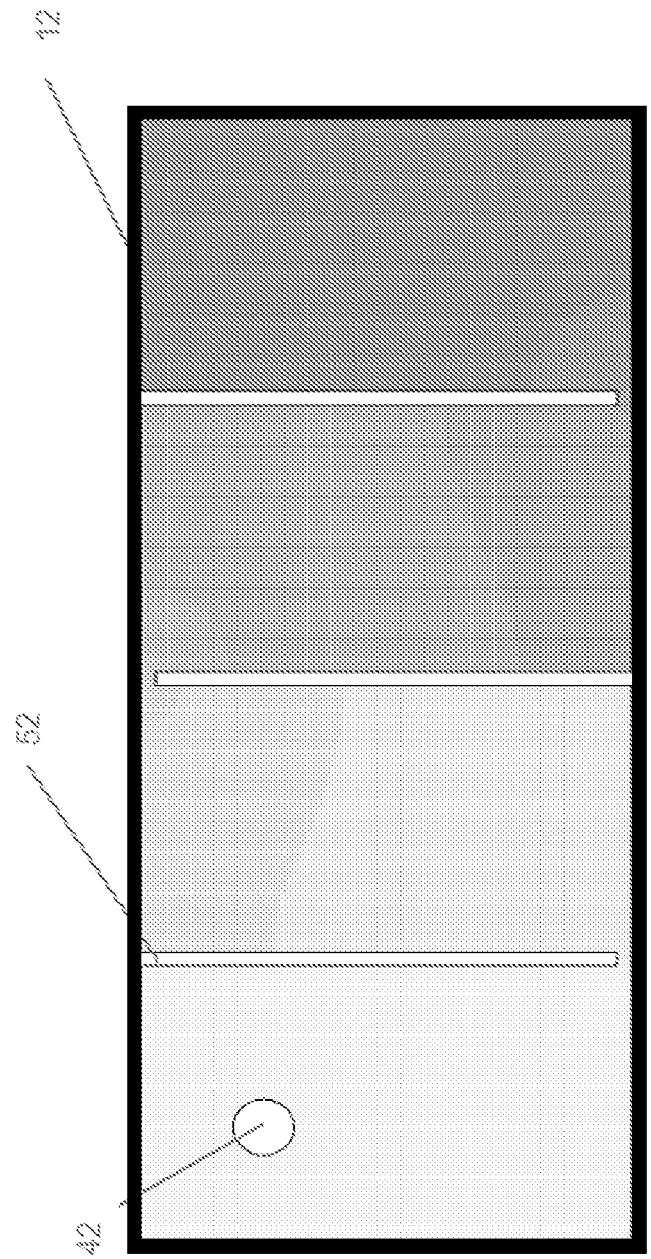
Fig. 23I

DRUG ELUTING COMPOSITE

CROSS-REFERENCE TO RELATED APPLICATIONS

This application is a continuation application of co-pending U.S. application Ser. No. 13/103,885 filed May 9, 2011, which is a continuation-in-part application of U.S. Pat. No. 9,320,890, filed Nov. 8, 2010, which is a continuation-in-part application of U.S. application Ser. No. 12/909,609, filed Oct. 21, 2010 and claims priority to U.S. Provisional Application No. 61/259,491, filed Nov. 9, 2009.

FIELD OF THE INVENTION

The present invention relates to medical devices and materials capable of releasing a therapeutic agent.

SUMMARY OF THE INVENTION

The present invention relates to materials capable of releasing a therapeutic agent contained within the invention at determined concentrations over determined periods of time. Pathways are present within the material of the invention for therapeutic agents to traverse. The pathways extend or alter the distance therapeutic agents contained within the invention must travel to exit the invention. The time taken for therapeutic agents to exit the invention is also extended or affected by the pathways. Pathways are established in the present invention with combinations of permeable and impermeable compositions and/or structures located within the material containing the therapeutic agents. Compositions and/or structures impermeable to a selected therapeutic agent are also used as barriers to the therapeutic agent on at least portions of one or more surfaces of the invention. As a result, the therapeutic agent can only exit the invention in areas not covered, contacted, or otherwise constructed with compositions and/or structures impermeable to the selected therapeutic agent. Openings are also provided in the compositions and/or structures impermeable to a selected therapeutic agent in some embodiments of the invention.

In alternative embodiments, pathways are established in the present invention with combinations of permeable and semi-impermeable compositions and/or structures located within the material containing the therapeutic agents. Semi-impermeable compositions and/or structures serve as barriers or other impediments to movement of therapeutic agents through the invention. As a result, the therapeutic agent will pass more slowly through the semi-impermeable compositions and/or structures than through the permeable compositions and/or structures.

Embodiments of the present invention allow for the tailored delivery of therapeutic compositions. In some embodiments such tailoring may be effected by altering the dimensions, compositions, characteristics, and placement of the impermeable or semi-impermeable compositions and/or structures without altering the starting amount or distribution of therapeutic agent present in the embodiment.

Embodiments of the present invention can be used alone or in combination with other embodiments of the invention. The invention can also be a component of a device such as cardiac pacing devices, cardiac defibrillation devices, neurostimulation devices, endoprostheses such as stents, grafts and stent-grafts, patches, drug delivery devices, such as oral or transdermal delivery patches and venous or arterial wraps, interventional devices such as catheters and filters, thrombectomy devices, diagnostic devices such as transducers, sensors, and other medical devices placed in proximity to living tissue and/or fluids targeted by one or more therapeutic agents. Embodiments of the present invention may be used in combination with medical devices placed within or on the body for short or long periods of time.

Implantable embodiments of the invention can be used to elute an anti thrombogenic drug into a specific location within the body such as to the left atrial appendage or other vascular site. Prevention of blood clots in the region of the left atrial appendage could obviate the need for a left atrial appendage occluder. In this embodiment, the therapeutic composition, agent, or compound in the present invention could be incorporated into an implantable embodiment and elute a high concentration of therapeutic when implanted which is subsequently rapidly diluted when the blood is washed out into the heart and circulatory system.

Such implantable embodiments of the present invention can also be constructed to elute therapeutics over more extended periods of time.

Accordingly, one embodiment of the present invention relates to a therapeutic-releasing material comprising a first biocompatible polymeric material having at least one surface and a therapeutic agent releasably incorporated in at least a portion thereof, wherein a portion of said first biocompatible polymeric material is impermeable to said therapeutic agent, and a second biocompatible polymeric material impermeable to said therapeutic agent covering substantially all said at least one surface.

Another embodiment of the present invention relates to a therapeutic-releasing material comprising a porous biocompatible polymeric material having at least one surface, a therapeutic agent releasably admixed with a biocompatible fluoropolymeric copolymer and incorporated in pores of said porous biocompatible polymeric material, wherein a portion of said porous biocompatible polymeric material is impermeable to said therapeutic agent, and a non-porous biocompatible polymeric material impermeable to said therapeutic agent covering substantially all said at least one surface.

A further embodiment of the present invention relates to a first biocompatible polymeric material in the form of a film having at least one surface and a therapeutic agent releasably incorporated in at least a portion of said film, wherein a portion of said first biocompatible polymeric material is impermeable to said therapeutic agent, and a second biocompatible polymeric material impermeable to said therapeutic agent covering substantially all said at least one surface of said film.

Other embodiments of the present invention relate to medical devices having a therapeutic-releasing material incorporated therein. For example, one embodiment relates to a cardiac pacing or Intracardiac Cardioverter Defibrillation (ICD) leads comprising a cardiac lead element having a proximal end and a distal end, an electrically conductive connector at said proximal end, an electrode located at said distal end, at least one electrically conductive element connecting said connector to said electrode, and at least a portion of said cardiac element covered with a therapeutic-releasing material having a first biocompatible polymeric material having at least one surface and a therapeutic agent releasably incorporated in at least a portion thereof, wherein a portion of said first biocompatible polymeric material is impermeable to said therapeutic agent and a second biocompatible polymeric material impermeable to said therapeutic agent covering substantially all said at least one surface.

Another embodiment relates to an electrically conductive lead comprising a lead element having a proximal end and a distal end, an electrically conductive connector at said proximal end, an electrode located at said distal end, at least one electrically conductive element connecting said connector to said electrode, a tubular lead tip located at said distal end, and at least a portion of said lead element covered with a therapeutic-releasing material having a first biocompatible polymeric material having at least one surface and a therapeutic agent releasably incorporated in at least a portion thereof, wherein a portion of said first biocompatible polymeric material is impermeable to said therapeutic agent and a second biocompatible polymeric material impermeable to said therapeutic agent covering substantially all said at least one surface.

In each embodiment of the present invention, at least one opening can be placed in the impermeable materials and/or impermeable portions of the invention to provide a path for therapeutic agents to be released from, or otherwise travel through, the material.

BRIEF DESCRIPTION OF THE DRAWINGS

FIG. 8A illustrates an embodiment of the present invention.

FIG. 8B illustrates a transverse cross section taken at the line "A" in FIG. 8A.

FIG. 9A illustrates an embodiment of the present invention.

FIG. 9B illustrates a transverse cross section taken at the line "B" in FIG. 9A.

FIG. 13 illustrates an embodiment of the present invention.

FIGS. 22A-22J depict therapeutic agent concentration over T=2.5 days for the constructions in FIGS. 14A-14J.

FIGS. 23A-23I depict therapeutic agent concentration over T=20 days for the constructions in FIGS. 14A-14I.

FIGS. 27A and 27B depict therapeutic agent concentrations at T=22.5 hours for FIGS. 25A and 17A, respectively.

DETAILED DESCRIPTION OF THE INVENTION

Figure 1:
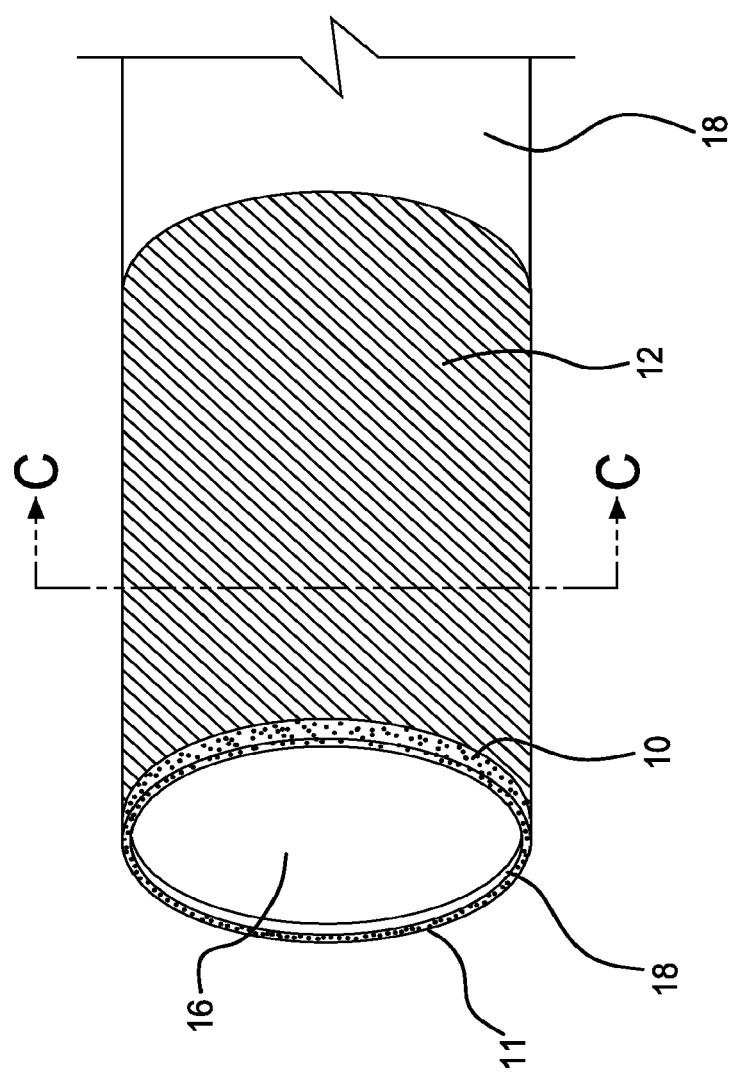
FIG. 1 illustrates a perspective view of an embodiment the present invention.

The present invention relates to materials having therapeutic compositions releasably contained within the materials. The materials are configured to release therapeutic compositions at a desired rate. The present invention also relates to devices incorporating the materials. In preferred embodiments, materials and/or constructions bar, or otherwise impede, movement of therapeutic compositions present within the material of the invention. Some embodiments have materials and/or constructions reducing, or otherwise limiting, the rate of release of therapeutic compositions from the invention, but not barring, blocking, or otherwise impeding movement of a therapeutic composition through the invention.

The rate at which therapeutic agents are released from the invention is influenced by several factors. These include the chemical composition of the components of the invention, the physical relationship of the components, the overall shape of the invention, and any openings provided in the invention. The chemical composition of the components of the invention include formulations of the therapeutic agent and materials containing the therapeutic agent, such as mass fractions, presence or absence of expedients, and the magnitude of the diffusion coefficient for the invention.

Combinations of compositions and/or structures permeable to therapeutic agents and compositions and/or structures impermeable to therapeutic agents are used in the present invention to establish a pathway along which therapeutic agents move as the agents move through and out of the invention. As a result, therapeutic agents are preferentially eluted, or otherwise released, from permeable portions of the material and not impermeable portions. In some embodiments semi-permeable compositions and/or structures can be used as partial barriers or other partial impediments to movement of therapeutic compositions through the invention.

A notable advantage of the invention is the ability to control the release rate concurrently with the total percentage of therapeutic compositions released. Some therapeutic compositions are unstable and it is not desirable to leave large or even small portions of the compositions remaining within the invention for periods of time. With more traditional approaches, the rate of release is controlled through the mixture of the therapeutic compositions and a polymer. Unfortunately, this can be problematic for systems in which long term release is desired with little or no remaining drug left behind. Long periods of release often mean using high polymer mass fractions relative to the drug in order to create a low drug diffusion coefficient. Such systems inherently entrap portions of the drug that remain within the drug delivery system permanently or longer than desired. What is needed is a system with low polymer mass fractions (and conversely high diffusion coefficients) that release drug over a long period with little drug retention. High diffusion coefficients for small molecules are around $10^{-4}$ to $10^{-8}$ cm$^2$/sec, with a medium range of $10^{-8}$ to $10^{-8}$ cm$^2$/sec, and at the low end at below $10^{-9}$ cm$^2$/sec. These ranges may trend downward as molecular weight of molecules increases substantially. Unlike the present invention, therapeutic compositions can remain within a conventional device permanently or for undesirable periods of time.

In addition, the invention has a variety of configurations which can influence the rate at which therapeutic agents are released from the invention. The configurations include films, sheets, rods, tubular shapes having luminal spaces, hollow or solid spherical shapes, laminates, wraps, and other shapes.

The material of the present invention includes therapeutic compositions, agents, drugs, or compounds, including but not limited to: small molecule drugs; large molecule drugs; medicaments; cardiovascular agents; chemotherapeutics; antimicrobials; antibiotics (e.g., dactinomycin (actinomycin O) daunorubicin, doxorubicin, and idarubicin), anthracyclines, mitoxantrone, bleomycins, plicamycin (mithramycin) and mitomycin); anesthetics; alkaloids (nicotine); hemostatics; antihistamines; antitumor agents; antilipids; antifungals; antimycotics; antipyretics; antirestenotics (e.g., pimecrolimus, cytochalasin, dicumarol, cyclosporine, latrunculin A, methotrexate, tacrolimus, halofuginone, mycophenolic acid, genistein, batimistat, dexamethasone, cudraflavone, simvastatin, prednisolone, doxorubicin, bromopyruvic acid, cilostazol, carvedilol, mitoxantrone, tranilast, etoposide, hirudin, trapidil, mitomycin C, abciximab, cilostazol, irinotecan, estradiol, diaziquone, dipyridamole, melatonin, colchicine, nifedipine, vitamin E, paclitaxol, diltiazem, vinblastine, verapamil, vincristine, rapamycin (e.g., Albumin-Bound (Nab)-Rapamycin (Abraxane), angiopeptin, everolimus, heat shock proteins, zotarolimus, nitroglycerin, prednisone); antimitotics/antiproliferatives (e.g., including natural products such as vinca alkaloids (e.g., vinblastine, vincristine, and vinorelbine), paclitaxel, epidipodophyllotoxins (e.g., etoposide, teniposide), alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC)); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (e.g., estrogen); vasodilators; hypertensive agents; oxygen free radical scavengers; vitamins; antivirals; analgesics; antiinflammatories (e.g., adrenocortical steroids (cortisol, cortisone, fludrocortisone, prednisone, prednisolone, 6a-methylprednisolone, triamcinolone, betamethasone, and dexamethasone, dexamethasone sodium phosphate, dexamethasone acetate, beclomethasone dipropionate); non-steroidal agents (e.g., salicylic acid derivatives such as aspirin); para-aminophenol derivatives e.g., acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone; gold compounds (auranofin, aurothioglucose, gold sodium thiomalate); diagnostic agents; visualization agents; angiographic contrast agents; peptides; proteins; antibodies (e.g., britumomab (Zevalin), bevacizumab (Avastin), rituximab (Rituxan), Cetuximab (Erbitux), Ofatumumab (Arzerra), Panitumumab (Vectibix), Trastuzumab (Herceptin), and Tositumomab (Bexxar)); enzymes (e.g., L-asparaginase); antiplatelet agents (such as G(GP)IIbIIIa inhibitors and vitronectin receptor antagonists); insulin; phase contrast agents, and radiopaque agents; thrombolytics intended to facilitate the breakup of thrombus; anticoagulants (e.g., heparin, synthetic heparin salts and other inhibitors of thrombin), intended to prevent thrombosis; fibrinolytic agents (such as tissue plasminogen activator, streptokinase and urokinase), aspirin, dipyridamole, ticlopidine, clopidogrel, abciximab; antimigratories; antisecretories (e.g., breveldin); immunosuppressives: (cyclosporine, tacrolimus (FK-S06), sirolimus (rapamycin), azathioprine, mycophenolate mofetil); angiogenic agents: vascular endothelial growth factor (VEGF), fibroblast growth factor (FGF); angiotensin receptor blocker; nitric oxide donors; anti-sense oligionucleotides and combinations thereof; cell cycle inhibitors, mTOR inhibitors, and growth factor signal transduction kinase inhibitors; RNA; viruses; and combinations thereof.

In a preferred embodiment of the present invention, a film material permeable to a therapeutic compound is impregnated or coated with a copolymer into which has been admixed the therapeutic compound. The preferred film material is an expanded polytetrafluoroethylene (ePTFE) construction. The copolymer is preferably a tetrafluoroethylene/perfluoroalkylvinylether (TFE/PAVE) copolymer, and more preferably a tetrafluoroethylene/perfluoromethylvinylether (TFE/PMVE) copolymer, made generally as taught by U.S. Pat. No. 7,049,380, and US Publication 20040024448 to Chang et al., both incorporated by reference herein. The resulting coated film may become less-permeable and preferably impermeable to the therapeutic compound. In some instances the permeability of the film may not change.

In some embodiments, a material impermeable to the therapeutic composition, agent, or compound is placed on at least one surface of the therapeutic-containing, coated film material as a "capping layer" to prevent movement of the therapeutic agent or compound through or out of the invention at the location of the impermeable material. The material for the "capping layer" is preferably formed of a polymer such as a silicone composition. Depending on the embodiment, the capping layer material is applied either to a portion of the coated film material or all of the film material. The portion of the coated film material which is not covered by the capping layer material preferentially elutes the therapeutic composition, agent, or compound when exposed. The capping layer material may be applied over the coated film material after the film material is applied to a substrate.

In some embodiments, the impermeable material, be it a "capping-layer" or a coated film has at least one opening therein.

In some embodiments, the present invention is combined with a substrate in the form of a device or other construction. In these embodiments, a coated film material is applied to all or a portion of the substrate underlying the invention. The coated film material may be cut into a tape and applied by wrapping the tape around the substrate. The tape is wrapped spirally, helically and/or longitudinally around at least a portion of the substrate. An adhesive may be used as needed to adhere the spirally-wrapped layers of film. If the coated film is "capped" with a capping layer which prevents elution from the coated film construct, the capping layer may also serve as an adhesive. The coated film may be applied to the substrate with the coated side facing the substrate or facing away from the substrate. Substrates may include tubes, rods, pellets, or any other three dimensional object, including substrates which may be a component of an assembled device. Substrates may be made of metals, polymers, and the like. The substrate may be shaped or altered to form elution pathways through and out of the present invention.

As used herein, the term "bioabsorbable" refers to a physiological process in which at least a portion of a material hydrolyzes, degrades, or otherwise dissolves in living tissue or biological fluid.

As used herein, the term "permanent implant" refers to a medical device intended to be implanted in a patient for all or most of the life of the patient.

As used herein, the term "semi-permanent implant" refers to a medical device intended to be implanted in a patient for less than most of the expected life of the patient. Semi-permanent implants are often accessed following implantation for removal of the device or other procedure related to the device.

Referring to FIG. 1, coated film (10) has a therapeutic composition, agent, or compound (not shown) incorporated with a film. Coated film (10) is applied over a substrate (18). A capping layer (12) is applied over coated film (10). The capping layer (12) is either made of materials impermeable to the particular therapeutic composition, agent, or compound or constructed to be impermeable to the particular therapeutic composition, agent or compound.

In this embodiment, the substrate (18) is a tubular structure with a luminal space (16). Material of the capping layer (12) covers only a portion of the coated film material (10) thereby leaving a portion of coated film material exposed around an edge, or lip, of the substrate (18). The exposed portion of the coated film material (10) has a thickness dimension (11).

Figure 1A:
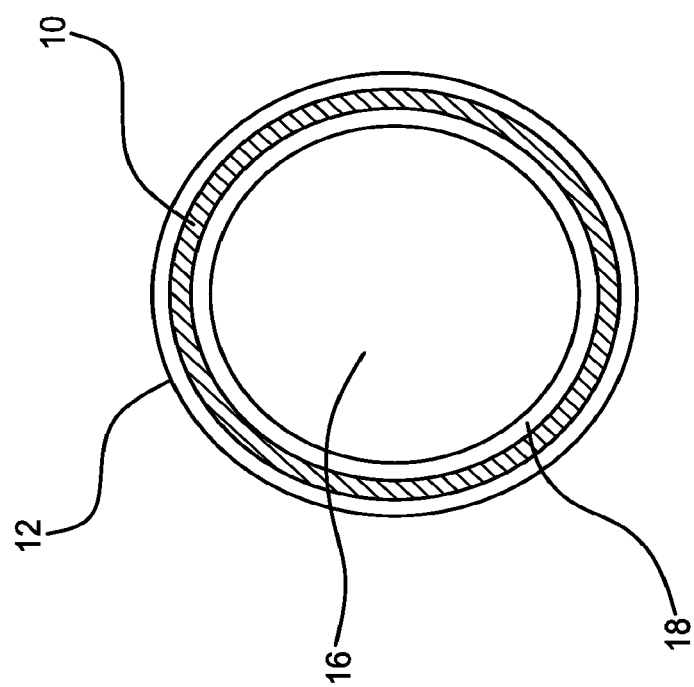
FIG. 1A illustrates a transverse cross section taken at line "C" in FIG. 1.

This embodiment is also illustrated in FIG. 1A as a transverse cross section taken at line "C" in FIG. 1 showing substrate material (18), luminal space (16), coated film material (10) and capping layer material (12).

In practice, the embodiment illustrated in FIG. 1 is placed in contact with or in proximity to a bodily tissue or fluid. Once in contact with tissue and/or fluid, the therapeutic composition, agent, or compound (not shown) contained within coated film (10) is preferentially eluted from those portions of the coated film material not covered by material of the capping layer (12). In this embodiment, for example, the therapeutic composition, agent, or compound elutes or otherwise exits the invention from an uncapped, or otherwise uncovered, edge (11) surrounding the opening of luminal space (16). The therapeutic composition, agent, or compound in the coated film material (10) may diffuse, or otherwise migrate, from portions of the coated film material (10) covered by material of the capping layer (12) and exit the invention from uncovered and exposed areas of the coated film material (10).

Figure 2:
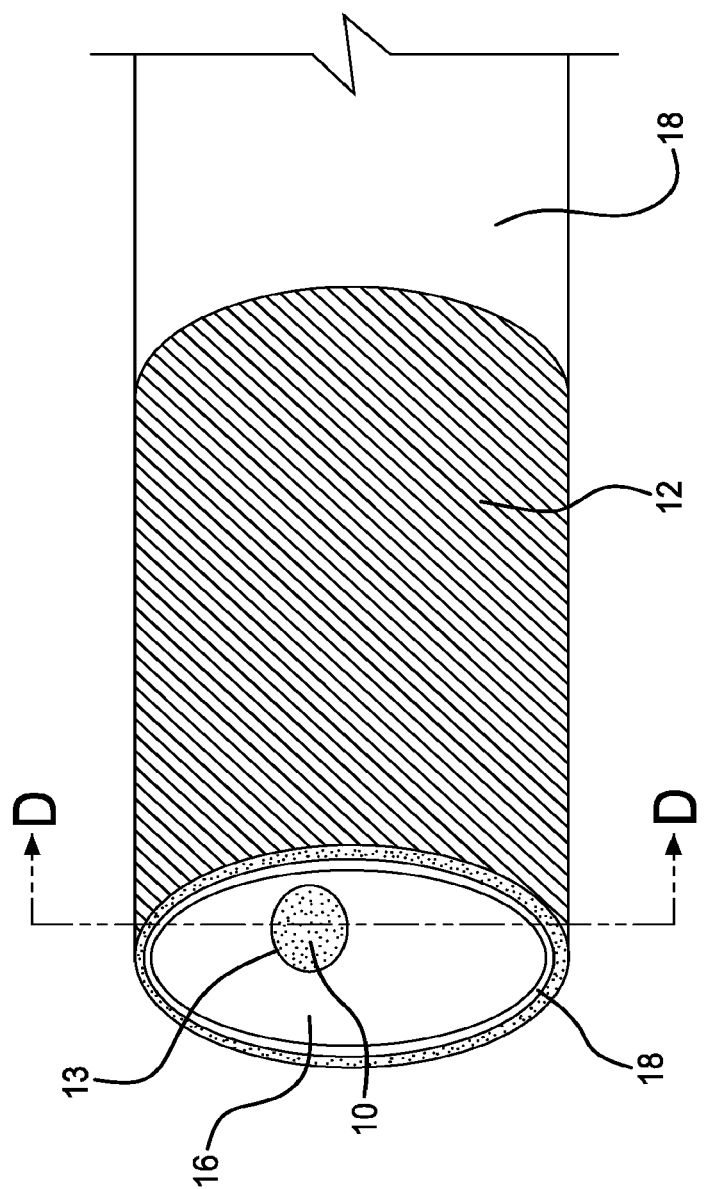
FIG. 2 illustrates a perspective view of another embodiment of the present invention.

Another embodiment of the present invention is illustrated in FIG. 2. In this embodiment, coated film material (10) has a therapeutic composition, agent, or compound (not shown) incorporated into the film. The coated film material (10) is applied over a substrate (18). A capping layer material (12) is applied over the entire exterior surface of coated film material (10). The capping layer (12) is either made of materials impermeable to the particular therapeutic composition, agent, or compound or constructed to be impermeable to the particular therapeutic composition, agent, or compound. An opening (13) in the form of a hole is made through substrate 18, exposing coated film material (10) to the luminal space (16) of the substrate (18). A porous material may be placed over opening (13) and between the substrate (18) and coated film material (10). Additionally, this material placed over opening (13) may modulate release of a therapeutic composition, agent, or compound.

Figure 2A:
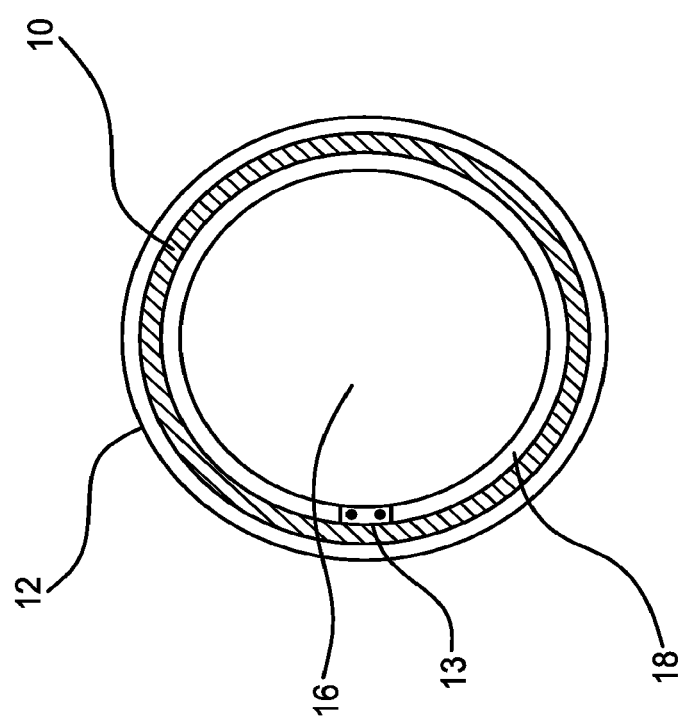
FIG. 2A illustrates a transverse cross section taken at line "D" in FIG. 2.

FIG. 2A is a transverse cross section taken at line "D" in FIG. 2 showing substrate (18), luminal space (16), coated film material (10), capping layer material (12), and opening (13).

In practice, the embodiment illustrated in FIG. 2 is placed in contact with or in proximity to a tissue or fluid. Once in contact with tissue and/or fluid, the therapeutic composition, agent, or compound in coated film material (10) preferentially elutes through opening (13) and into luminal space (16) including surrounding fluid and/or tissues (not shown). The therapeutic composition, agent, or compound in coated film material (10) may migrate to opening (13) from portions of coated film material (10) covered by capping layer material (12) and located away from opening (13).

Figure 3:
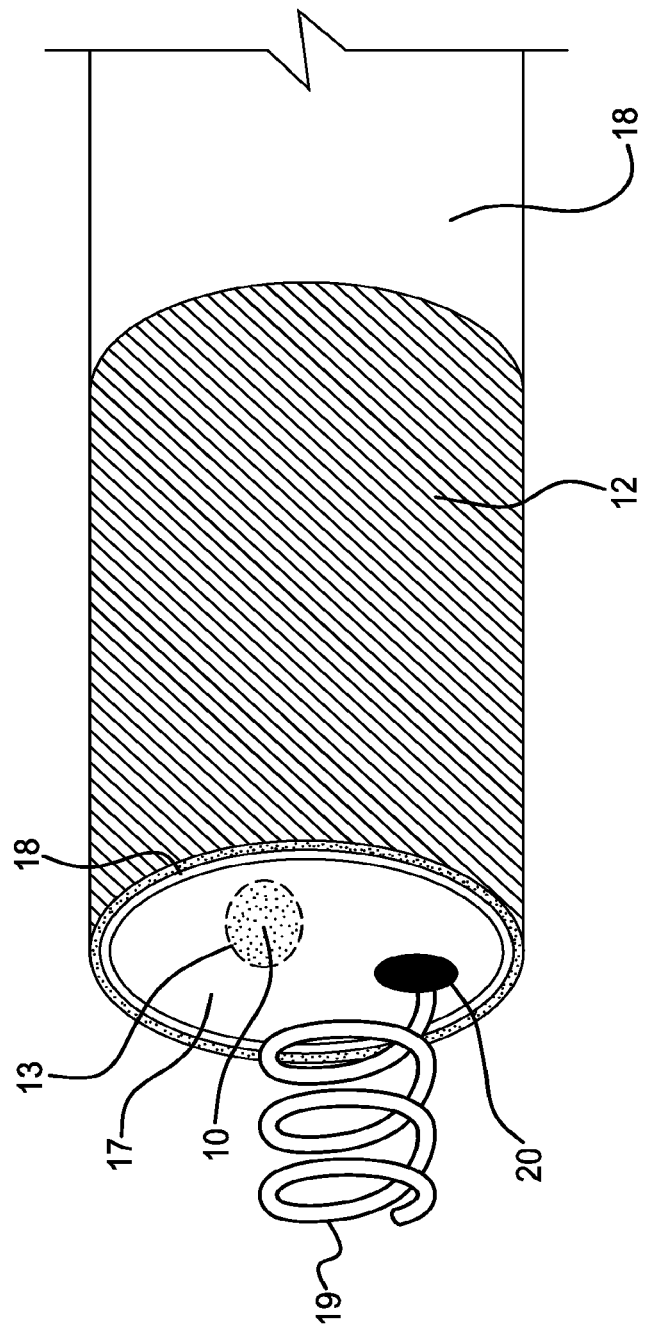
FIG. 3 illustrates a perspective view of the embodiment of FIG. 2.

FIG. 3 is a perspective view of the embodiment illustrated in FIG. 2 except a cover material (17) covers luminal space (16) as shown in FIG. 2. Optionally, an opening (20) can be made in cover material (17) through which tissue fixation means (19), such as a screw, may be included. Additional means of tissue fixation include appropriate anchors, barbs, hooks or adhesives. The tissue fixation means can be made of metallic or polymeric materials. The metallic or polymeric materials can be bioabsorbable or non-bioabsorbable. An example of a bioabsorbable metal is magnesium. An example of a bioabsorbable polymer is polyglycolic acid commonly known as PGA.

In practice, the embodiment illustrated in FIG. 3 is anchored into tissue using tissue fixation screw (19) and the therapeutic composition, agent, or compound in coated film material (10) is allowed to preferentially elute from opening (13) into luminal space (16) and out of opening (20) into surrounding tissues and/or fluids. The embodiment illustrated in FIG. 3 may be used for implantation into the heart and other tissues as described below. For example, in cardiac leads a tissue fixation screw (19) is often placed into the septum of the right ventricle.

Figure 4:
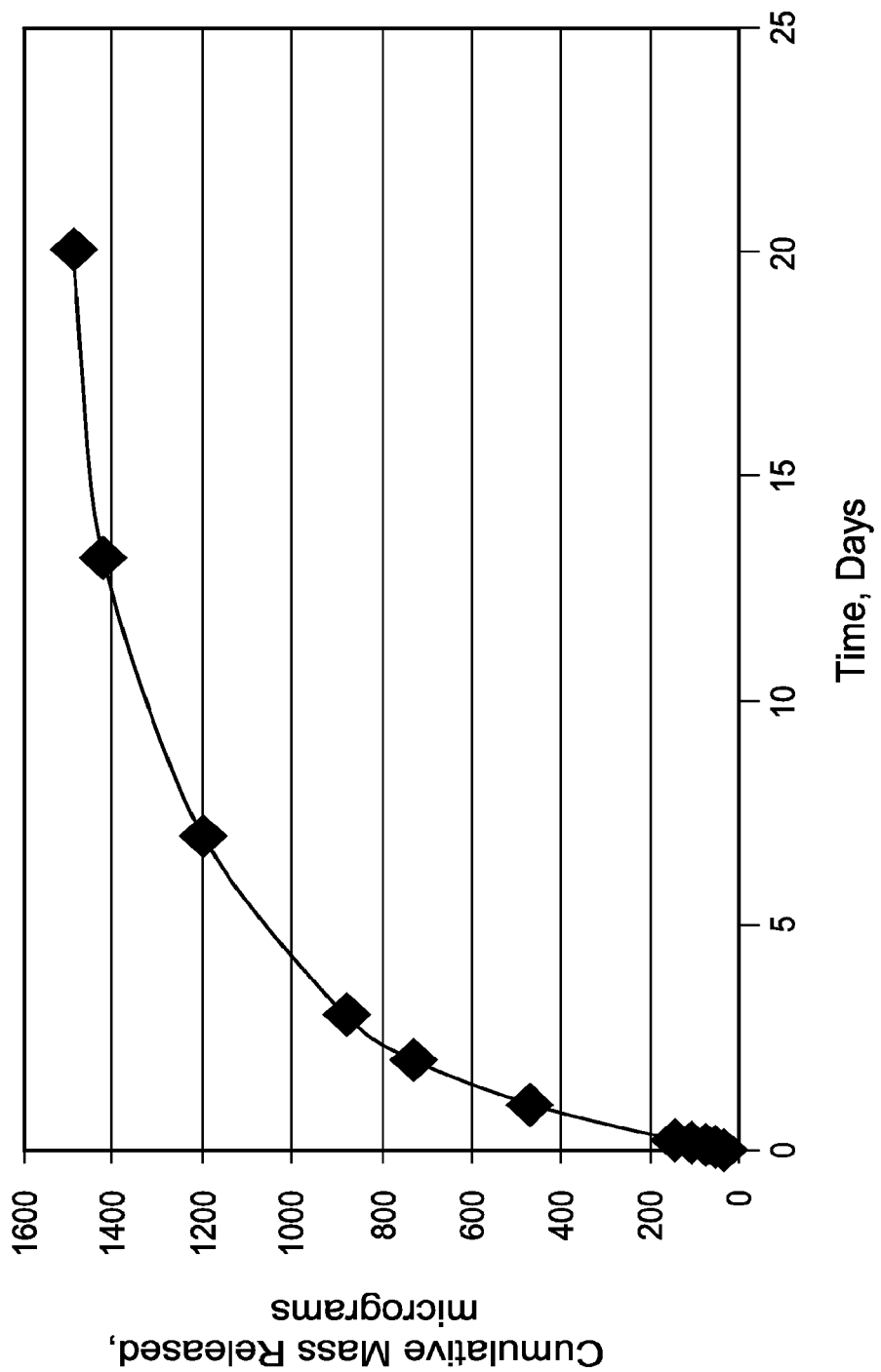
FIG. 4 is a graph.

FIG. 4 is a graph of the cumulative mass of drug released as a function of time for the embodiment described in Example 1.

Figure 5:
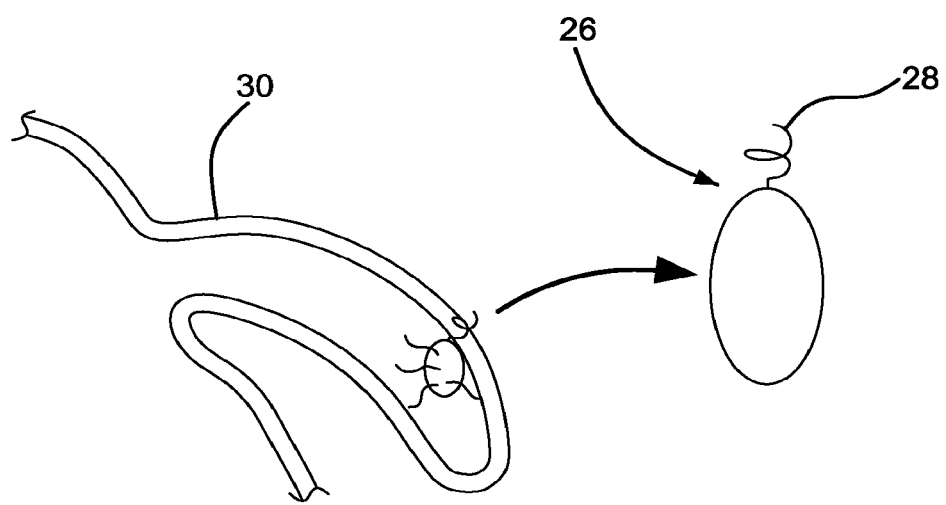
FIG. 5 illustrates an embodiment of the present invention.

FIG. 5 illustrates another embodiment of the present invention. A housing (26) includes a therapeutic eluting construction of the present invention with a means to attach the housing (26) to tissue such as a tissue attachment screw (28). Depending on the application, the housing (26) may be attached to a tissue region or anatomical location such as a left atrial appendage (30). The attachment may be permanent or semi-permanent in the event the housing (26) is subsequently removed and optionally exchanged.

Figure 7:
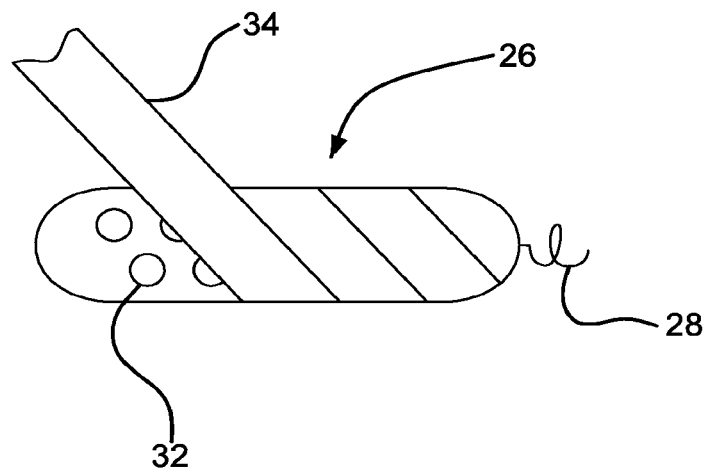
FIG. 7 illustrates an embodiment of the present invention.

The housing (26) may be incorporated in the embodiment described in Example 1. The housing (26) may be made of metallic or polymeric materials. The housing (26) is solid, hollow, or includes features such as perforations (32) as illustrated in FIG. 7.

In one embodiment, both a housing (26) and tissue attachment screw (28) are made of materials which are bioabsorbable. In one embodiment, the entire housing (26) is a solid bioabsorbable material having a therapeutic composition, agent, or compound incorporated therein. Over time, the entire housing implant will hydrolyze, or otherwise dissolve, while eluting the therapeutic agent. In yet another embodiment, the therapeutic composition, agent, or compound incorporated within the bioabsorbable material may vary in both composition and concentration. For example, the housing (26) may be constructed such that the initial eluted dosage of therapeutic composition, agent, or compound may be very high, with potency dropping off over time as a function of variable bioabsorption produced by using materials of varying bioabsorbability. In one embodiment, such variable elution may be utilized by constructing a housing (26) with multiple layers of therapeutic-loaded bioabsorbable materials, each layer having a different therapeutic concentration or each layer having a different rate of bioabsorbability, or a combination of both.

Elution rates may also be varied by modifying the housing (26). For example, the housing (26) may include perforations (32) as illustrated in FIG. 7. The perforations (32) permit elution from the inner regions of the housing (26) or increase surface area of the housing (26). In one embodiment, elution rates may be controlled by overwrapping or encasing a housing (26) within a porous or semi-permeable covering material (34) as illustrated in FIG. 7. A porous expanded polytetrafluoroethylene (ePTFE) material exhibits biocompatibility and substantial chemical inertness. A porous expanded polytetrafluoroethylene material for the overwrapping or encasing material is a preferred material.

Figure 6:
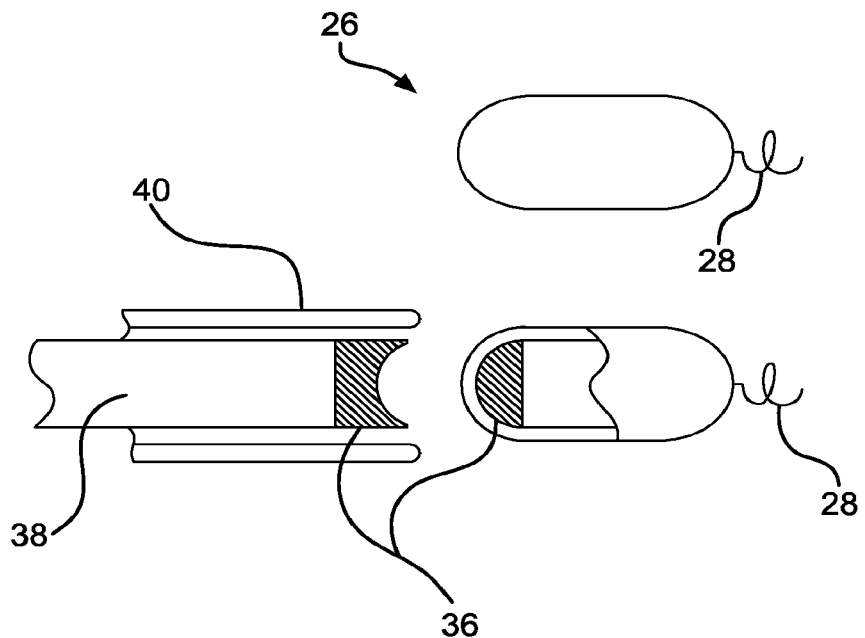
FIG. 6 illustrates a means for delivery or retrieval of the invention.

In some situations, it may be necessary to retrieve or replace an implanted embodiment of the present invention. Retrieval can be accomplished with a grasping tool. In one embodiment, a magnetic attachment is used to retrieve or replace an implanted device (see e.g., FIG. 6). Magnets (36) may be embedded within or on the surface of the housing (26) and the associated catheter (38). The magnets (36) are configured to exert an attractive force between the magnets. Once a sufficient magnetic attraction has been established, in-situ capture and movement of housing (26) can be performed. A sheath (40) may be used in the present invention. The sheath (40) is advanced over a housing (26) and the entire system rotated to cause release of the tissue attachment screw (28) and removal from the implant site.

Embodiments of the present invention may be configured for a variety of purposes, including therapeutic-eluting tips for cardiac pacing or Intracardiac Cardioverter Defibrillation (ICD), or neurostimulation leads; or other therapeutic-eluting devices for placement in proximity to other body tissues. Once placed at the desired location by interventional or surgical means and enclosed by tissue or affixed to tissue with an anchor, the invention can be of therapeutic value by locally or systemically delivering a drug. Although the left atrial appendage (30) implantation site is described herein, it should be appreciated that the present invention may be applicable to a variety of other applications, such as in or proximate various organs, e.g., the liver, kidney, brain; or peripheral vascular system. Accordingly, use of the present invention need not be constrained to the cardiovascular system. For instance, embodiments for implantation within a sinus cavity and loaded with an antihistamine or other allergy-symptom relieving agent are contemplated. Additional embodiments include drug delivery devices for oral or transdermal implantation or fixation which are loaded with a therapeutic agent, like insulin.

FIG. 8A illustrates an embodiment of the present invention. Referring to FIG. 8A, therapeutic-releasing construction (40) is comprised of a biocompatible material, for example a coated film (10), a "capping layer" or impermeable material (12), and an opening (42) extending through impermeable material (12). Therapeutic-releasing construct (40) may be constructed to be any dimension but could be constructed to have a length of about 2 cm with a width of about 0.8 cm. The capping layer (12) may be of any thickness. A thickness of about 0.01 mm may be used. While shown as surrounding all of coated film (10), the capping layer (12) may surround only a portion of coated film (10). Coated film (10) may be of any thickness. A thickness of 0.5 mm may be used. Opening (42) may be formed by avoiding covering a portion of coated film (10) or by cutting through capping layer (12) by means as known in the art. Opening (42) may act as a diffusion barrier to further modulate release by providing a cover of permeable material over opening. Opening (42) may be of any dimension and shape. An opening (42) with the shape of a circle and the diameter of about 1 mm may be used. More than one opening may be used. The opening (42) may be placed at any location through impermeable material (12).

The rate at which therapeutic agents are released from therapeutic-releasing construction (40) will vary should the amount or dimensions of coated film (10) be varied, or the size or position of opening (42) be altered.

It will be understood that instead of using coated film (10) a therapeutic composition, agent, or compound, including one incorporated in a matrix, for example a polymer, could also be used in embodiments of the present invention.

This embodiment is also illustrated in FIG. 8B as a transverse cross section taken at line "A" in FIG. 8A showing coated film (10) and capping layer material (12) and opening (42).

In practice, the embodiment illustrated in FIG. 8A-8B is a therapeutic-releasing construction or material (40) that may be applied to a variety of medical devices or used in vivo for therapeutic composition, agent, or compound delivery as discussed previously. If applied to a medical device, placement of the opening (42) may be manipulated to be in contact with tissue and/or fluid. Once in contact with tissue and/or fluid, the therapeutic composition, agent, or compound (not shown) contained within coated film (10) is preferentially eluted from those portions of the construction (40) not covered by material of the capping layer (12). In this embodiment, for example, the therapeutic composition, agent, or compound elutes or otherwise exits the invention from the illustrated opening (42). The therapeutic composition, agent, or compound in the coated film (10) may diffuse, or otherwise migrate, through portions of the coated film (10) covered by material of the capping layer (12) and exit the invention from uncovered and exposed areas of the coated film (10).

FIGS. 9A and 9B illustrate an embodiment of the present invention with FIG. 9B being a transverse cross section taken at line "B" in FIG. 9A. Referring to FIGS. 9A and 9B, therapeutic-releasing construction (50) is constructed as described for the embodiment in FIGS. 8A and 8B with a coated film (10), a "capping layer" or impermeable material (12), and an opening (42) extending through impermeable material (12). A barrier material (52) which may be impermeable or semi-permeable to the particular therapeutic composition, agent, or compound incorporated in coated film (10) is disposed within coated film (10). The height of barrier material (52) is shown in FIG. 9B as extending the full vertical distance between the capping layers (12) but may be dimensioned to extend only a portion of this distance. The length and/or width of barrier material (52) may be varied as well, as may the number of barriers (52).

In FIG. 9A (with upper capping layer (12) removed for clarity), barrier material (52) is shown extending from one edge of the coated film (10) toward a second edge and ending a distance away from said second edge. This distance alone or in combination with the number or dimensions of barrier materials (52) may be varied and can be used to tailor the transport or elution path of therapeutic agents through coated film (10) as is represented by a path of a theoretical molecule as illustrated in FIG. 9a as a dotted line with an arrow indicating the exit at the opening (42). Altering this elution pathway in any way may alter the elution rate of the therapeutic composition, agent, or compound. Elution pathways may also be altered by varying the orientation of the barrier material (52) as further illustrated in FIGS. 10-12.

In practice, the embodiment illustrated in FIG. 9A-9B may be used in vivo for therapeutic composition, agent, or compound delivery or applied to a substrate, for example a medical device as listed above.

Figure 10:
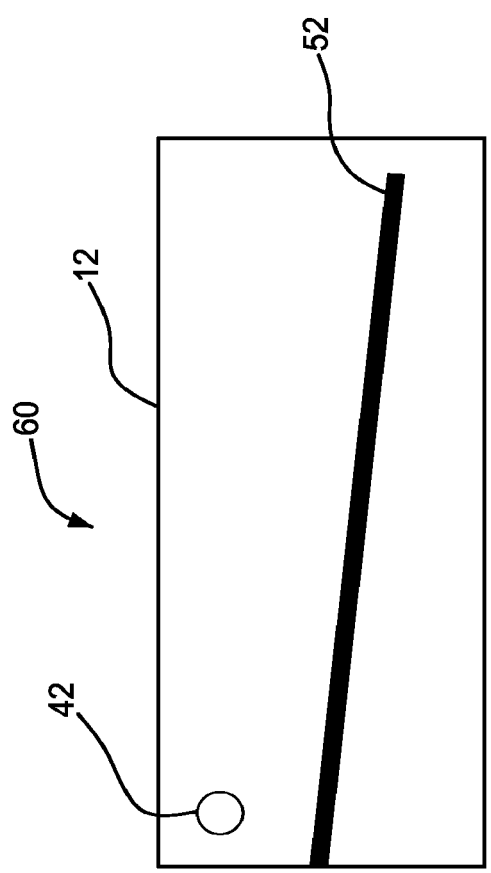
FIG. 10 illustrates an embodiment of the present invention.

FIG. 10 illustrates an embodiment of the present invention wherein the barrier material (52) has been positioned off the center line of therapeutic-releasing construction (60) and extending a longitudinal distance from one edge of coated film (10). Barrier (52) may also be placed at a location away from said edge. Any orientation of barrier material (52) may be employed. A barrier material (52) having an orientation of a non-zero angle off the longitudinal center line could be used. An orientation of about five degrees may also be used. As described previously, any length of barrier material (52) may be used. A length of barrier material (52) leaving about a 1 mm gap between the end of the barrier material (52) and edge of coated film (10) may also be used.

Depending on the shape, dimensions, and location of barrier materials (52), those portions of coated film (10) separated by barriers (52) may act as reservoirs for therapeutic compounds admixed or otherwise incorporated with coated film (10). Generally, the larger the volume of the separated portions of coated film (10) the more likely those portions are to serve as reservoirs. The smaller the volume the more likely the portions are to serve more as elution channels. When functioning as reservoirs, coated film volumes may contain different therapeutic compounds. For example in FIG. 10, the portion of coated film (10) above barrier (52) and proximate opening (42) could contain an anti-thrombogenic therapeutic and the lower portion of coated film (10), located below the barrier (52), could contain an anti-inflammatory. In use, the therapeutic-releasing construct (60) could be positioned proximate a vascular occlusion with the anti-thrombogenic therapeutic eluting through the nearest opening (42), eluting first to dissolve the occlusion and the anti-inflammatory agent eluting subsequently to lessen inflammation at the site of the lesion.

Figure 11:
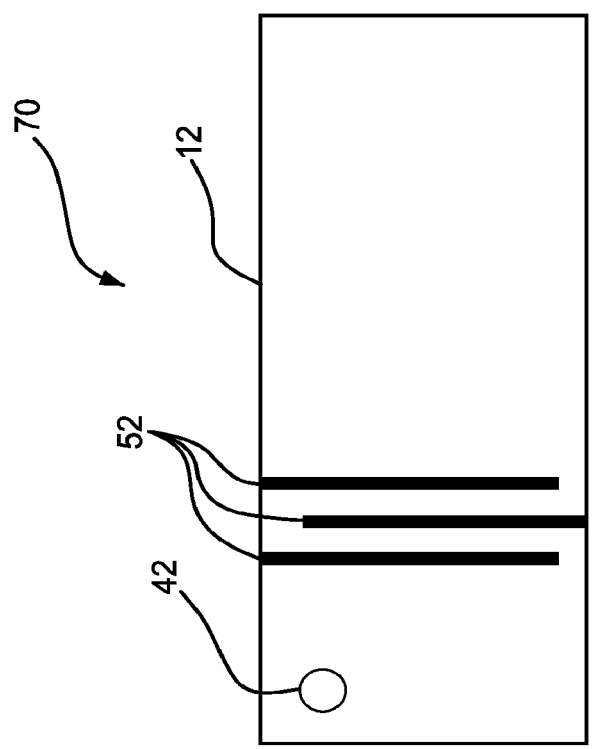
FIG. 11 illustrates an embodiment of the present invention.

FIG. 11 illustrates an embodiment of the present invention. FIG. 11 shows therapeutic-releasing construction (70) as previously described but with barrier materials (52) positioned perpendicular to the longitudinal center line of construction (70) and closer together than those shown in FIGS. 9A and 9B. This embodiment illustrates an elution pathway having these attributes: This embodiment provides a portion of therapeutic compound in close proximity to the opening with no barriers for a burst release followed by a longer release time for the majority of therapeutic compound contained beyond the barriers (i.e., to the right of the last barrier (52) in FIG. 11). The three barriers illustrated in FIG. 11 greatly extend the pathway for the therapeutic compound to travel. Moving the barriers closer to the opening will reduce the burst release of therapeutic compound and result in more therapeutic compound being released later in time. Having the barriers relatively close together results in a small amount of therapeutic compound between the barriers effectively creating two reservoirs. Spacing them further apart can create a four reservoir system as illustrated in FIG. 9A.

Figure 12:
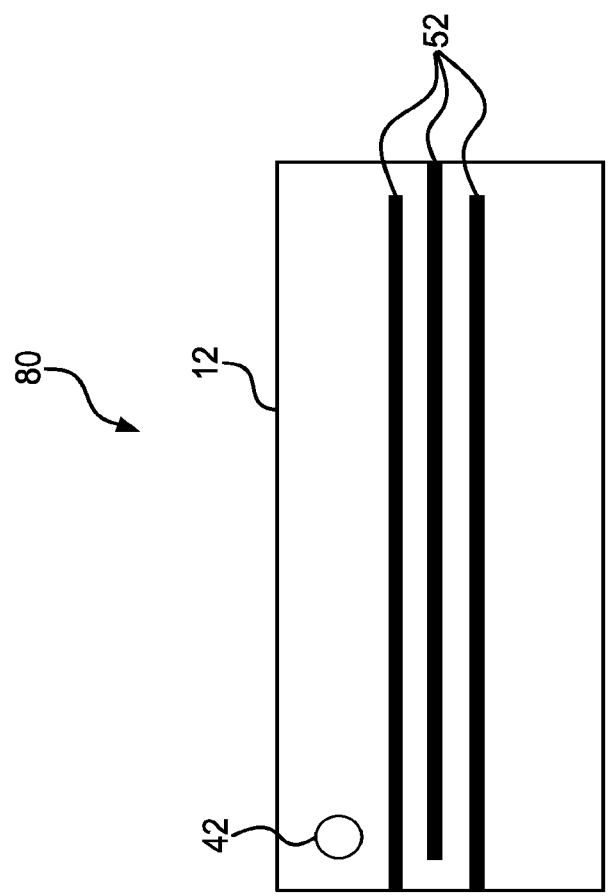
FIG. 12 illustrates an embodiment of the present invention.

FIG. 12 illustrates an embodiment of the present invention. FIG. 12 shows therapeutic-releasing construction (80) as previously described but with barrier materials (52) positioned parallel to the longitudinal center line of construction (70) and placed close to one another. This embodiment illustrates an elution pathway longer than those shown in FIGS. 9 through 11. In this embodiment, the therapeutic compound is released for the longest period of time, relative to the other constructions. As previously described, the amount of therapeutic compound released earlier or later can be tailored by moving the barriers closer or further away from the hole, respectively. Spacing the barriers further apart will alter the size of areas of the coated film (10) serving as therapeutic agent reservoirs.

FIG. 13 shows a cross section of therapeutic-releasing construct (90) as previously described but barriers (52) have been created by fusing a portion of the opposing capping layers (12) together after removing coated film (10). This construct may be achieved by using various methods known in the art. For example, coated film (10) may be placed on the capping layer (12) which includes outlet (42). Then desired portions of the coated film (10) are removed, for example, with a laser. Then capping layers (12) are added to all edges of therapeutic-releasing construct (90) and a capping layer (12) is added to the top of the construct, opposite the capping layer (12) with opening (42). The construct (90) is then placed into a die which presses a portion of the opposing capping layers (12) together, fusing them to create an impermeable barrier (52). In addition to pressure, the fusing together of portions of the capping layers (12) may be augmented by application of heat or adhesives to the areas where coated film (10) has been previously removed. It will be understood that the shape and dimensions of impermeable barrier (52) can be varied to achieve the desired eluting pathway(s).

Figure 14A:
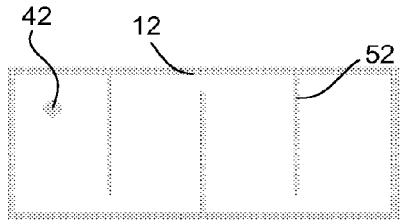
FIGS. 14A-14J illustrate constructions having various barrier configurations in accordance with exemplary embodiments of the present invention.
Figure 14B:
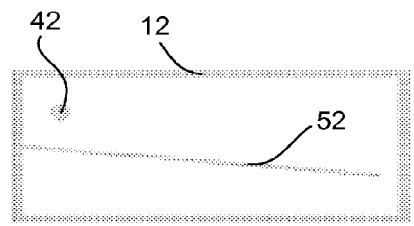
Figure 14C:
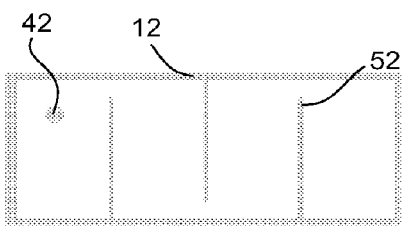
Figure 14D:
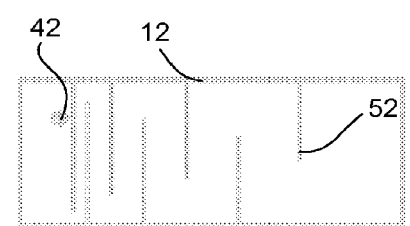
Figure 14E:
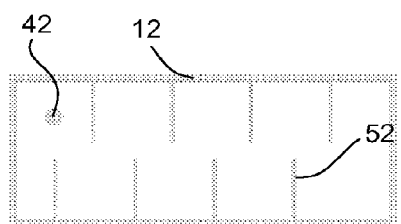
Figure 14F:
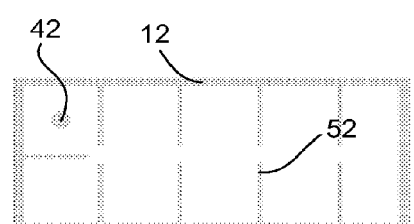
Figure 14G:
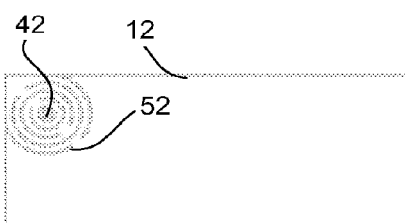
Figure 14H:
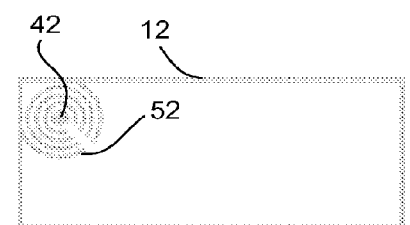
Figure 14I:
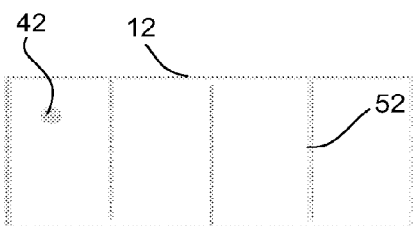
Figure 14J:
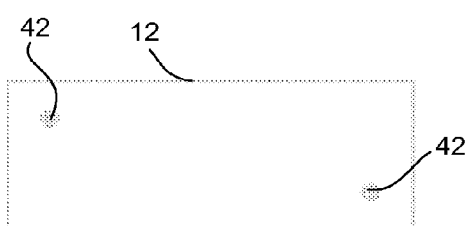

Additional embodiments of therapeutic-releasing constructions of the invention are illustrated in FIGS. 14A-14J, each of which may comprise impermeable material (12), one or more openings (42), and one or more barriers or barrier materials (52), the latter labeled only once in each Figure for clarity and simplicity. (Note that FIGS. 14A and 14B are substantially similar to FIGS. 9A and 10 respectively.) FIGS. 14A and 14C differ in the orientations of barriers (52) to opening (42), with the longer elution distance of 14A contributing to a slower elution rate. FIGS. 14A and 14I differ in the size of the gaps between barriers (52) and the edge of impermeable material (12), with the larger gaps of 14A resulting in a faster elution rate. The large volume below barrier (52) in FIG. 14B may act as a reservoir, as previously described. Tight constriction near opening (42) in both FIGS. 14D, 14G, and 14H greatly reduces the elution rate. Similarly, the small opening (or "constriction" of the elution path) between the three barrier (52) ends closest to opening (42) in FIG. 14F decreases the elution rate, compared to that in FIG. 14E. The construction depicted in FIG. 14J shows constructions may have more than one opening (42), in this case two.

Importantly, the illustrated embodiments should not be construed as limiting, but rather examples of constructions which regulate elution rates and thus can be tailored for a wide range of drug delivery applications. Generally speaking, the present invention comprises therapeutic-releasing constructions having one or a plurality of therapeutic agent elution pathways defined by impermeable or semi-permeable materials, compositions, structures and/or barriers. In exemplary embodiments, impermeable or semi-permeable materials, compositions, structures and/or barriers provide for the manipulation of an elution rate without necessarily altering the base geometry or dimensions of the construction or altering the amount or type of therapeutic agent or altering the composition or dimensions of a coating or matrix in which a therapeutic agent may be carried.

Both relatively simple, as well as more complex, elution pathways having primarily x and y directional components (the z direction being significantly smaller than the x and y directional components) are contemplated herein, such as those illustrated. To name just a few, the proximity of the distance between barriers to the opening, the distance between barriers, the gaps between barrier ends and impermeable material edges or top/bottom/side walls, volume between barriers, constriction between barriers, staggering of barriers, orientation of barriers, dimensions of barriers, composition of barriers, permeability of barriers (should they be semi-permeable), shape of barriers, e.g., a barrier need not be straight as shown in the Figures but may be rounded, contoured, segmented and the like), and tortuosity can be adjusted to alter the elution rate. Tortuosity may be defined as the variability from a straight line of an elution pathway as affected by one or more well-placed impermeable or semi-permeable materials, compositions, structures and/or barriers. In addition, barriers need not be attached to or placed against adjacent impermeable materials but instead may be placed in the middle of a construction with elution occurring between the barrier ends and nearby impermeable material side walls, for example.

Additionally, a plurality of therapeutic-releasing constructions may be arranged such that one or more elution pathways extend in the z direction. In exemplary embodiments, one or more constructions are wrapped about or otherwise bonded or adhered to the interior and/or exterior of an implantable device to extend an elution pathway in the z direction, which may lengthen the diffusion length. A construction may be wrapped about or otherwise bonded or adhered to an implantable device in any number of configurations, for example, helically, sinusoidally, in a zig-zag configuration, a ladder configuration, etc.

Constructions need not be limited in their z-direction or thickness. Thicker coatings of drugs and/or matrices, along with higher barriers (in the z-axis) are also contemplated. Although not limited to such thicker constructs, barriers may be made to extend only partially between a lower and upper impermeable material. This in turn could be used to further tailor elution pathways in the z-axis.

Additionally, constructions of the present invention may be made to function themselves as medical devices. For example a flat or semi-flat construction of the invention may be surgically or percutaneously placed adjacent a tissue region into which one or more therapeutics are delivered in a tailored, controlled fashion. A flat construct may similarly be wrapped upon itself in a spiral and placed in the body for another form of controlled therapeutic agent elution.

Figure 15A:
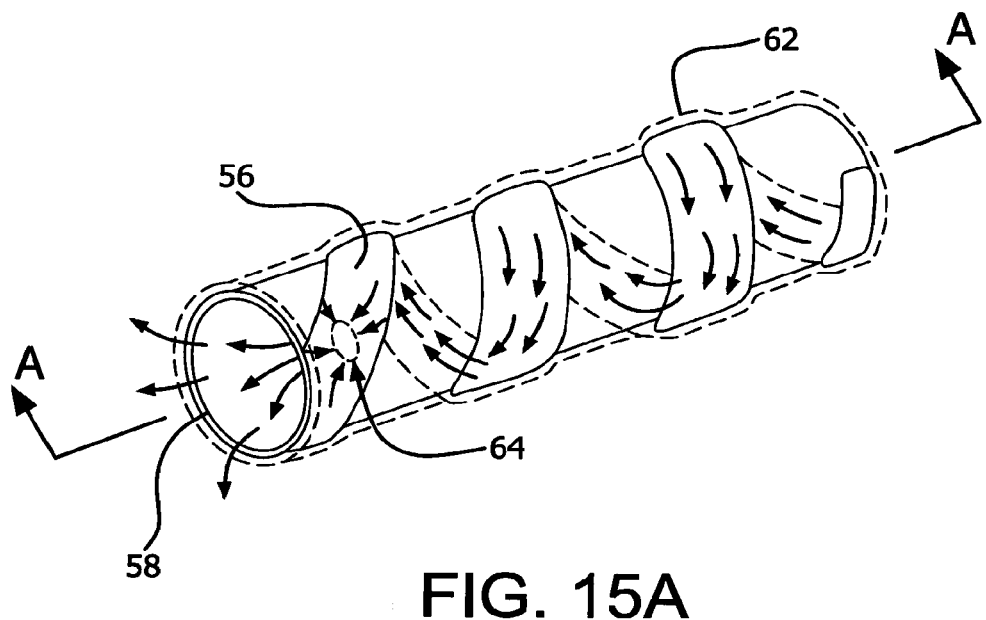
FIGS. 15A-15B illustrate embodiments comprising helically wrapped constructions.

In another embodiment, and with reference to FIG. 15A, a construction is helically wrapped about an implantable device to create a helical path, which may lengthen the diffusion length. This embodiment shows a therapeutic agent loaded strip (56) in a helix orientation attached to a solid impermeable substrate (58) on the inside and fully covered with a impermeable or semi-impermeable capping layer (62) on the exterior. Strip (56) is preferably porous to a drug or otherwise allows it to travel within strip (56). Capping layer (62) may comprise a polymer. In this configuration, the therapeutic agent must follow the helical path in the direction of the arrows to reach an elution opening (64) where the therapeutic agent can then elute into the inner diameter of solid impermeable substrate (58). In exemplary embodiments, changing the width of therapeutic agent loaded porous polymer strip (56) and the pitch of the pattern (helix) can be used to alter the total therapeutic agent loading, elution pathway, and therapeutic agent elution rate. In such embodiments, the spacing between therapeutic agent loaded porous polymer strip (56) can be created with a laser ablation or a die cutting process. Capping layer (62) may be attached over the full length of therapeutic agent loaded porous polymer strip (56) and solid impermeable substrate (58). In yet other embodiments, polymer non-porous capping layer (62) is attached over less than the full length. Optionally, porous polymer strip may contain barriers as previously described.

Figure 15B:
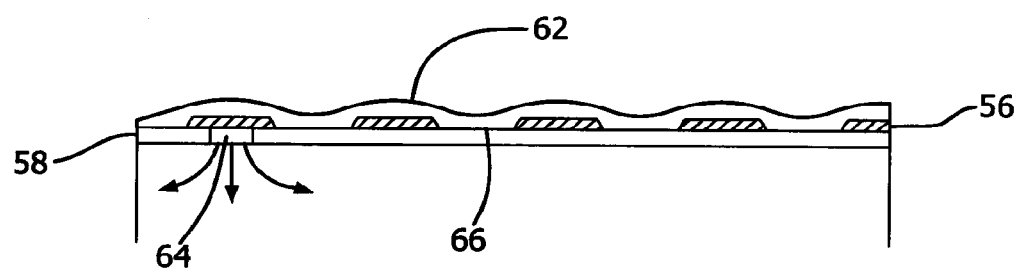

In another embodiment, and with reference to FIG. 15B which is a cross section A-A of FIG. 15A, rather than employing a laser ablation or die cutting process, polymer non-porous capping layer (62) can be bonded or adhered to solid impermeable substrate (58) with gaps (66) forming a helical barrier which will direct flow of the therapeutic agent elution through a helical pattern that is therapeutic agent loaded porous polymer strip (56) and thereby allow the agent to directly flow to elution opening (64) into the inner diameter of solid impermeable substrate (58) in the direction of the arrows.

Figure 16:
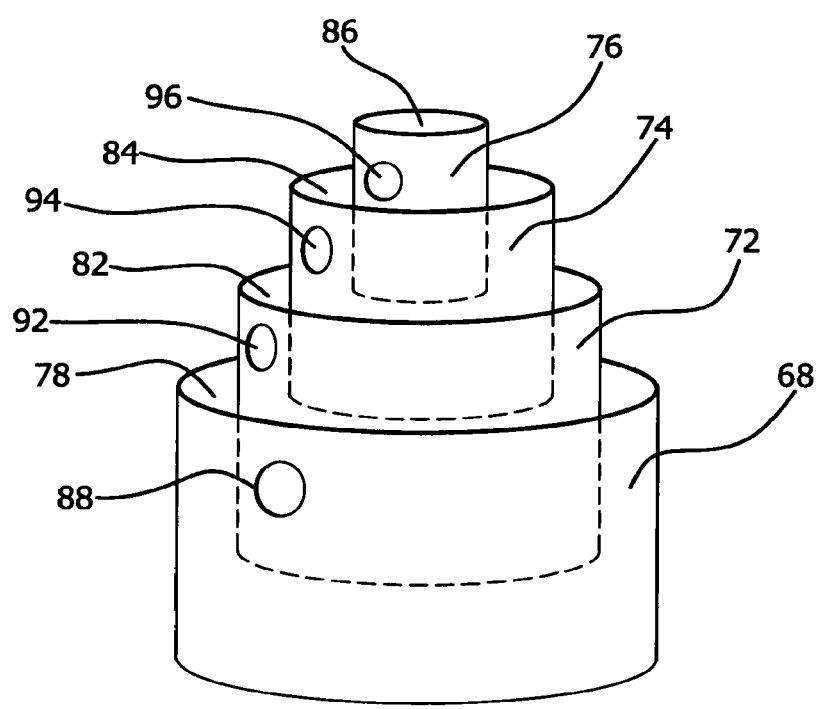
FIG. 16 illustrates embodiments comprising stacked or layered constructions.

In yet other embodiments, a plurality of constructions may be stacked in proximity to each other, for example, to deliver a plurality of therapeutic agents, or the same therapeutic agent but in different potencies (i.e., using different concentrations). In the embodiment shown in FIG. 16, construction cylinders (68), (72), (74), and (76) are stacked inside one another and contain therapeutic agents (78), (82), (84), and (86) respectively, and have elution pathways exiting at openings (88), (92), (94), and (96) respectively. This configuration provides for timed, mostly sequential elution of a plurality of therapeutic agents, or the same therapeutic agent but in different potencies, for example. Additionally, construction cylinders (68), (72), (74), and (76) may be rotated to align or offset openings (88), (92), (94), and (96) and thus alter the elution rate. Optionally, cylinders (68), (72), (74), and (76) may be formed as cups or enclosed on both open ends to form enclosed cylinders. Optionally, the cylinders may contain barriers as previously described. For example, the cylinders may be formed by bending the construction in FIG. 9A into a cylinder.

Figure 17A:
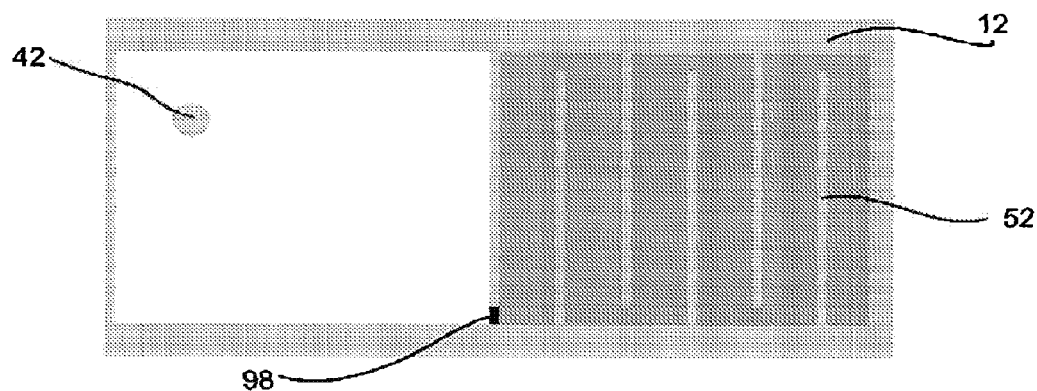
FIGS. 17A-17G illustrate exemplary constructions comprising gates and exemplary manners for opening gates.

A therapeutic-releasing construction may comprise one or more gates interjected in or otherwise creating a barrier to an elution pathway which are openable or may open and close. FIG. 17A, for example, illustrates a construction having impermeable material (12), opening (42), barrier material (52), and a gate (98). In this embodiment, an initial burst delivery of a therapeutic agent located in the volume on the left of gate (98) is followed by a slower delivery of a therapeutic agent contained in the volume and between the barriers (52) to the right of gate (98). Optionally, the therapeutic agents (or agent carriers) on each side of gate (98) may differ in type or concentration. Thus, one or more gates in an exemplary embodiment provides for a plurality of elution profiles which are, at least in part, controlled by actuation of a gate. In a preferred embodiment, a gate provides a reservoir for delivery of a therapeutic agent according to a different elution profile or for delivery at a later time. Gates may also be opened in a staged manner, for example, where an initial actuation allows release and subsequent actuations allow release of alternate therapeutic agents.

A plurality of elution pathways defined within a single construction, as described herein, may be useful in several respects, for example, to enable the delivery of a single therapeutic composition according to different elution rates, or to enable the delivery of multiple therapeutic compositions (or different potencies of a single therapeutic composition) according to the same or different elution rates.

Gates impeding pathways of therapeutic-releasing construction may be opened in various manners, including but not limited to a mechanical or electrical device, including inductive devices, by a bioabsorbable portion, mechanically, e.g., upon pressure applied to the body proximate the construction, by a weakened portion, or remotely (e.g., by transfer of energy such as magnetic and ultrasound energy, etc.). If constructions are used in association with electrically-powered devices, e.g., cardiac leads, gates may also be opened by application of electrical energy selectively shunted from the electrical device. Referring to FIG. 17A, in another embodiment, the top and bottom sides of the construction may be pinched together to close off gate (98) with a subsequent release of such pinching resulting in the return of top and bottom sides to their original position and the reopening of gate (98).

Figure 17B:
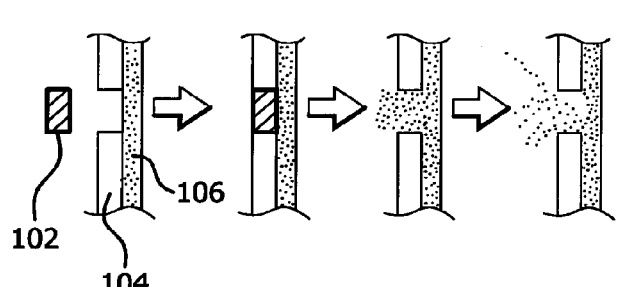

FIG. 17B illustrates an embodiment comprising a bioabsorbable or dissolving plug (102) occluding a gap between impermeable material (104) and thereby preventing elution of a therapeutic agent (106). As absorbable plug (102) decays over time, therapeutic agent (106) is released. Non permeable but absorbable or dissolvable plugs may be fabricated from absorbable metals such as magnesium or fine grain austenitic stainless steel. Polymeric bioabsorbable materials suitable for use include, but are not limited to, poly(DL lactide-co-glycolide) copolymers, polyglycolide, poly(DL lactide), poly(L lactide), polycaprolactone, polydioxanone, and polyhydroxybutyrate and the like.

Figure 17C:
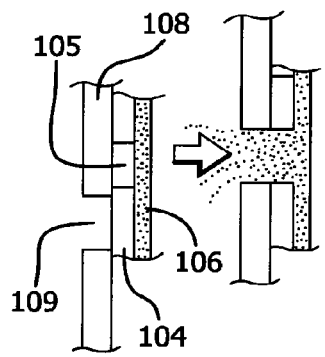

FIG. 17C illustrates an embodiment comprising a first impermeable material (104) and a second impermeable material (108), having holes (105) and (109) respectively completely or partially offset from one another, thereby preventing at least some elution of a therapeutic agent (106). First impermeable material (104) and second impermeable material (108) are moved relative to each other thereby aligning holes (105) and (109) and therapeutic agent (106) is released. Actuation may be accomplished in various manners. In a preferred embodiment, the construction is first impermeable material (104) and second impermeable material (108) wrapped ePTFE tubes having at least one helically-wrapped layer. Optionally, if more than one layer is used, the layers may be wrapped on an opposing bias. The first impermeable material (104) may act as an capping layer through which is placed a hole (105). The second impermeable material (108), which may be wrapped in the opposite direction of the first impermeable material (104), may serve as another capping layer also with an opening (109) or series of openings (109) cut in a particular location. When first impermeable material (104) tube and second impermeable material (108) tube are slide relative to one another, holes (105 and 109) align and therapeutic agent (106) is allowed to elute.

Figure 17D:
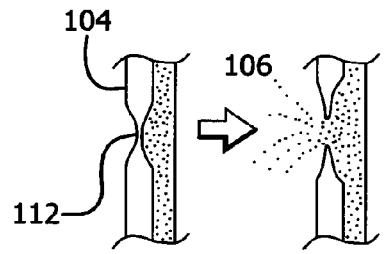

With reference to FIG. 17D, the construction may comprise an impermeable material (104) having a weakened zone (112) preventing elution of a therapeutic agent (106). Weakened zone (112) may be compromised mechanically, for example by a mechanical or electrical device pulling the weakened zone apart. In another embodiment, weakened zone (112) is compromised upon radial dilation about weakened zone (112). An example of a weakened zone in an ePTFE construct would be a thinned and densified area. A zone as such can easily be produced with proper heat and pressure using techniques commonly known to those skilled in the art of PTFE processing.

Figure 17E:
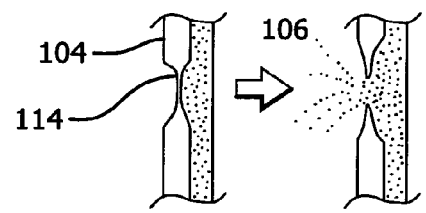

In a similar embodiment, and with reference to FIG. 17E, the construction may comprise an impermeable material (104) having a weakened zone (114) preventing elution of a therapeutic agent (106). In this embodiment, weakened zone (114) may be compromised remotely (e.g., by transfer of energy such as magnetic and ultrasound energy, shock waves, etc.). For example, in various embodiments of the present invention, ultrasound energy, as used in extracorporeal shock wave lithotripsy or similar techniques known to persons skilled in the art may be used to compromise weakened zone (114).

Figure 17F:
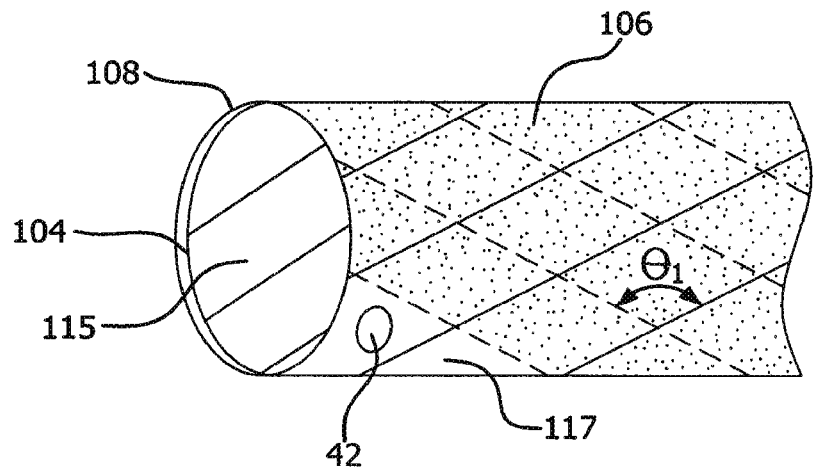
Figure 17G:
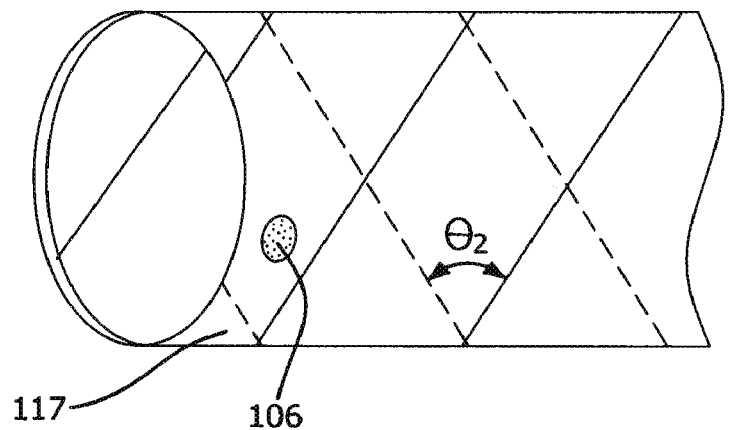

In another embodiment of the invention shown in FIGS. 17F-17G, a drug eluting construction comprises first impermeable material (104) formed as an inner tube which is located within a second impermeable material (108) formed as an outer tube. The assembly may include a lumen 115. A therapeutic agent 106 is applied to a part of the exterior surface of the inner tube. As shown in FIG. 17F, a portion (117) of the exterior of the inner tube is not coated with drug. A hole 42 (or holes) is created through the external tube. The hole is located such that in a first state the uncoated portion of the exterior of the inner tube is exposed through the hole. Each tube is constructed by helically wrapping a film tape around a mandrel. A preferred film material is ePTFE. The film tape wrappings overlap one another (overlaps not shown) but are not attached at the overlapped regions. Instead, the film wraps are secured at the ends of each tube. This allows the wraps to move relative to one another when a tube is radially torqued. Upon such torquing the tube expands (and may foreshorten). In the tube within a tube construct shown in FIG. 17G radial torquing of the two tubes opposite each other will cause both tubes to expand. At the same time, the wrappings in both tubes will slide radially relative to one another. Doing so changes the relative angle between the wrap angles on the first and second tubes. In FIG. 17F angle $\theta_1$ exists in a first, untorqued state and as shown in FIG. 17G a lesser angle $\theta_2$ is created when both tubes are radially torqued into a second, expanded state. This change in relative angle serves to move hole 42 from lying over the portion of the inner tube which is not coated with a drug to a portion of the inner tube which is coated. This, in turn, allows release of the drug from the construction.

Shape memory materials may also be incorporated to accomplish some of the objectives described herein. In addition to gates, barriers themselves may also be mechanically adjusted in vivo, at the patient bedside or during manufacture. For example, and with momentary reference back to FIGS. 14G and 14H, circular barriers (52) may be rotated to align or offset gaps between barriers and thus alter the elution rate. Additionally, in some embodiments, one or more elution pathways lead to a plurality of openings, for example, as illustrated in FIG. 14J.

In sum, elution pathways may be structurally configured in various ways to alter the elution rate of therapeutic compositions from construction openings. Depending on the pathway(s), wrapping, stacking, gate(s), barrier mobility, opening(s), etc., elution rates over time may be configured to be linear, curved, a polynomial of any degree, a combination thereof, etc. In like manner, elution rates may be configured to be continuous or intermittent with a constant or variable frequency. In preferred embodiments, elution rates are controlled without altering the base geometry or dimensions of the construction or altering the therapeutic agent.

Exemplary embodiments of the present invention may be configured to provide for elution of a therapeutic agent over a "short term" (i.e., less than 30 days) and/or over a "long term" (i.e., more than 30 days).

Depending on the application, the most appropriate elution rate(s) may depend upon a variety of factors, including one or more clinical indication(s), the patient, the specific location within the body, and the therapeutic composition to be delivered.

For example, a desired elution rate may comprise an initial burst delivery followed by delivery of a lower dosage over a short term, while another desired rate may comprise an initial delivery of a first therapeutic composition and a follow-up delivery of a second therapeutic composition. Yet another desired rate may comprise intermittent delivery over a long term and a reserve for later, controlled delivery by a medical practitioner. The present invention meets these needs.

Being able to manipulate elution rates, and to do so in a predictable manner by structurally altering elution pathways as described herein, thus has significant implications. In this regard, exemplary embodiments of the present invention further comprise methods for predicting elution rates for therapeutic-releasing constructions and related methods for designing constructions to provide desired elution rates.

Elution rates may be predicted analytically, using computational fluid dynamics ("CFD"), and/or experimentally, each of which may be used to validate the others. CFD solves conservation equations to predict the movement, or flux, of chemical species within the fluid and across defined boundaries.

In exemplary embodiments, predicting elution rates analytically may comprise using one or more equations taking into account one or more of the factors including geometry, tortuosity, the diffusion length, the diffusion coefficient, and the void volume. Equation (1) is such an equation suitable for simple geometries.

$$\frac{M_t}{M_\infty} = 1 - \sum_{n=0}^{\infty} \frac{8}{(2n+1)^2 \pi^2} e^{-D_e(2n+1)^2 \pi^2 t / 4\gamma^2} \quad (1)$$

Where $\tau$ is the tortuosity, $\gamma$ is the diffusion length, D is the diffusion coefficient, and the void volume is represented by $\varepsilon$ in Equation (2) such that:

$$D_e = \frac{D\varepsilon}{\tau} \quad (2)$$

Predicting elution rates in exemplary embodiments using CFD may comprise modeling a construction geometry and meshing the model with an appropriate interval size of elements. An interval size may be from about $5\times10^{-5}$ m to about $1\times10^{-3}$ m, more preferably from about $4\times10^{-4}$ m to about $1\times10^{-4}$ m, and most preferably about $4\times10^{-4}$ m. Elements are preferably quadrilateral (4-node), triangular (3-node), or a combination thereof. Predicting elution rates in this manner may further comprise applying appropriate boundary conditions and assigning material properties, which may include density, viscosity, molecular weight, and the diffusion coefficient. In exemplary embodiments, some of the boundary conditions and material properties are kept constant as not having as much impact as other variables, for example, the geometry, tortuosity, the diffusion length, and the void volume.

Figure 18:
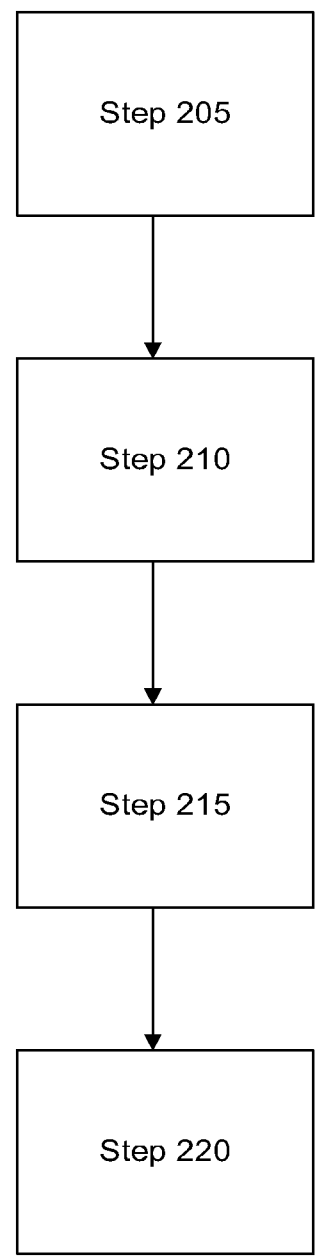
FIG. 18 illustrates a flow chart of an exemplary method of the present invention.

Constructions may be designed by structurally altering elution pathways in ways believed (whether known or predicted analytically, using CFD, and/or experimentally) to provide desired elution rates. By way of a non-limiting example, and with reference now to FIG. 18, an exemplary method comprises a step 205 of identifying a therapeutic composition, a step 210 of identifying a desired elution rate, a step 215 of designing a therapeutic-releasing construction, and a step 220 of verifying that the therapeutic-releasing construction will deliver the therapeutic composition according to the desired elution rate.

The step of designing may comprise altering one or more of the proximity of the gaps between barriers to the opening, the size of the gaps between barriers, gaps between barrier ends and side walls, volume between barriers, constriction between barriers, staggering of barriers, orientation of barriers, and shape of barriers. In addition to alterations to pathway(s), designing may further comprise wrapping, stacking, gate(s), barrier mobility, opening(s), etc. The step of verifying may be accomplished analytically, using CFD, and/or experimentally, as described above.

An exemplary method may further comprise a step of re-designing a therapeutic-releasing construction if it can not be verified that the therapeutic-releasing construction will deliver the therapeutic composition according to the desired elution rate.

EXAMPLES

Example 1

A copolymer of tetrafluoroethylene/perfluoromethylvinylether (TFE/PMVE) as described in EP 1545642 B1 was obtained in a 0.12 wt % solution of Fluorinert FC-77 (3M, St Paul, Minn.). To this solution was added an appropriate amount of dexamethasone sodium phosphate (Spectrum, Gardena, Calif.) to produce a solution of 0.12 wt % of the drug. The solution was sonicated to ensure complete mixing.

An expanded polytetrafluoroethylene (ePTFE) film tape of approximately 0.01 mm in thickness and 0.8 cm width was utilized in the manufacturing of the drug release system. A length of ePTFE film tape approximately 8 cm long was mounted onto a flat sheet of aluminum foil with a section of adhesive tape at each end. The ePTFE film tape was spray-coated with the TFE/PMVE and dexamethasone sodium phosphate solution using an airbrush (Badger standard set, model 350 (Badger Air Brush Co., Franklin Park, Ill.) set at 220 KPa gauge air pressure. Spray coating was conducted for 2-3 minutes, the coating was allowed to air dry, and the coated film then coated again. This was continued until the coating mass added to the tape was approximately 1 mg per 1 cm length. The opposite side of the film tape was left uncoated.

A metal tube of outside diameter of 1.50 mm, length 3 cm was obtained. A thin layer of a substantially non-porous composite film including expanded polytetrafluoroethylene (ePTFE) with a thermal adhesive layer of ethylene fluoroethylene perfluoride on one side was applied to the tube extending approximately 0.8 cm back from the tip of one end. This construction was utilized as a model cardiac pacing lead tip. The end of a segment of the coated film tape of 0.8 cm width and 2 cm in length was attached to the outer circumference of the tube, with the drug coated side facing the tube, at its end utilizing a silicone adhesive (MED-137, NuSil Technology, Carpinteria Calif.) and allowed to fully cure. After curing, a spatula was used to spread a thin film of the silicone adhesive on the coated side of the coated tape, and the tape was wrapped with the coated side toward the tube. The wrapped coated tape was then capped on a portion of its outer surface using silicone applied with a spatula, while not coating a thin strip of approximately 1 mm or less in width adjacent to the opening of the coated tape wrapped metal tube. The construction was allowed to cure overnight.

Constructions so made possessed a theoretical drug loading of approximately 2 mg and were tested for determination of drug release. A construction was placed in a vial containing 3 ml of PBS and maintained in a 37 degree C. incubator. Samples of 3 ml were taken at various time points and the vial replenished with fresh PBS to maintain the volume at 3 ml. Drug concentration was measured on an UV spectrophotometer at 242 nm. The graph shown in FIG. 4 demonstrates an extended elution time for the drug dexamethasone sodium phosphate.

Example 2

Figure 19A:
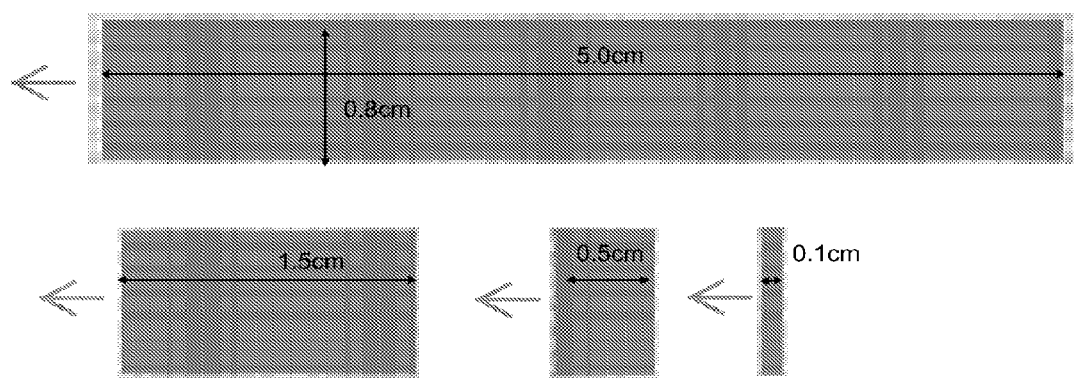
FIG. 19A illustrates simple geometry constructs for validating an exemplary CFD analysis.
Figure 19B:
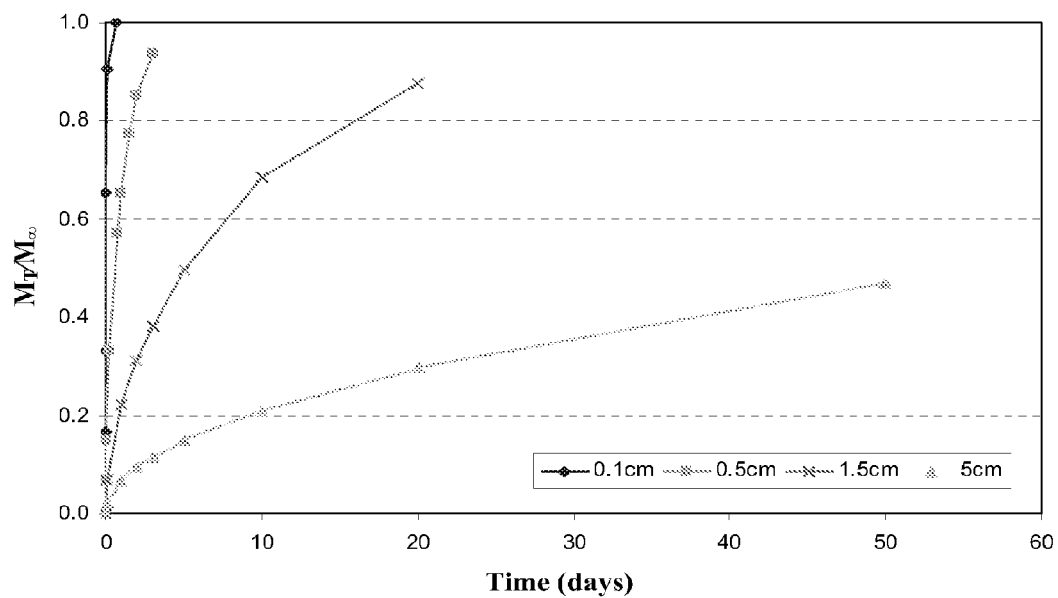
FIGS. 19B and 19C are plots depicting analytical and CFD elution rates respectively for the geometry constructs shown in FIG. 19A.

In this example, analytical solutions for elution rates across the four simple geometries shown in FIG. 19A were generated from Equation (1), according to methods described in Crank, J., 1975, The Mathematics of Diffusion, Oxford University Press., which is hereby incorporated by reference in its entirety for all purposes. The analytical elution rates are depicted in FIG. 19B.

Figure 19C:
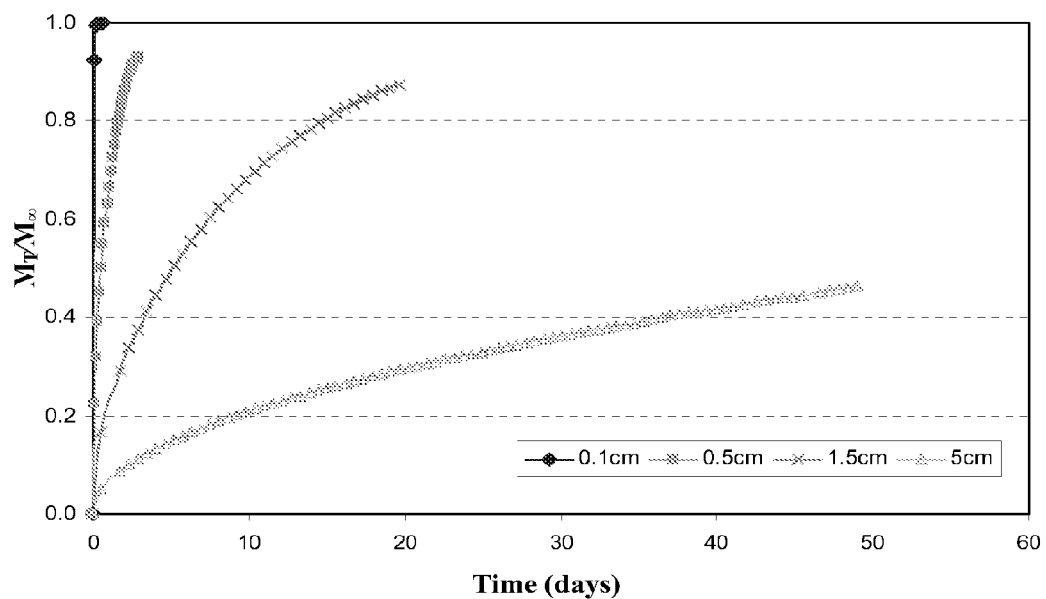

Next, a CFD analysis was developed and used to generate solutions for elution rates across the same four simple geometries. The construction geometries were modeled in two dimensions (because of the assumption that the thickness of the model is significantly smaller than the x- or y-dimensions, which is well-supported with the validation presented) and the models were meshed utilizing SolidWorks 2010 SP3.0 and Ansys 12.1. A triangular (3-node) mesh was selected with an interval size of $4 \times 10^{-4}$ m. Appropriate boundary conditions were applied and material properties were assigned. There was a zero diffusive flux across the walls, so that diffusion only occurred at the outlets of each geometry, the outlets being the left hand edges or faces of each geometric construct. Diffusion from each outlet is indicated by the arrows in FIG. 19A. The convective term at the outlet was also neglected. Initially the entire geometry was assumed to be coated with the drug so that the there were no voids, and the concentration of the drug at the outlet was zero. The density, viscosity, and molecular weight for each species were set to 1 and the diffusion coefficient was set to $1 \times 10^{-6}$ cm$^2$/s. The CFD elution rates for the four simple geometries shown in FIG. 19A were generated utilizing Fluent 12.1.4 and are depicted in FIG. 19C.

The CFD analysis was then validated against the analytical solutions by comparison. The CFD solutions were compared to the data generated by Equation (1) and found to match within 3% of the series solution.

Figure 20:
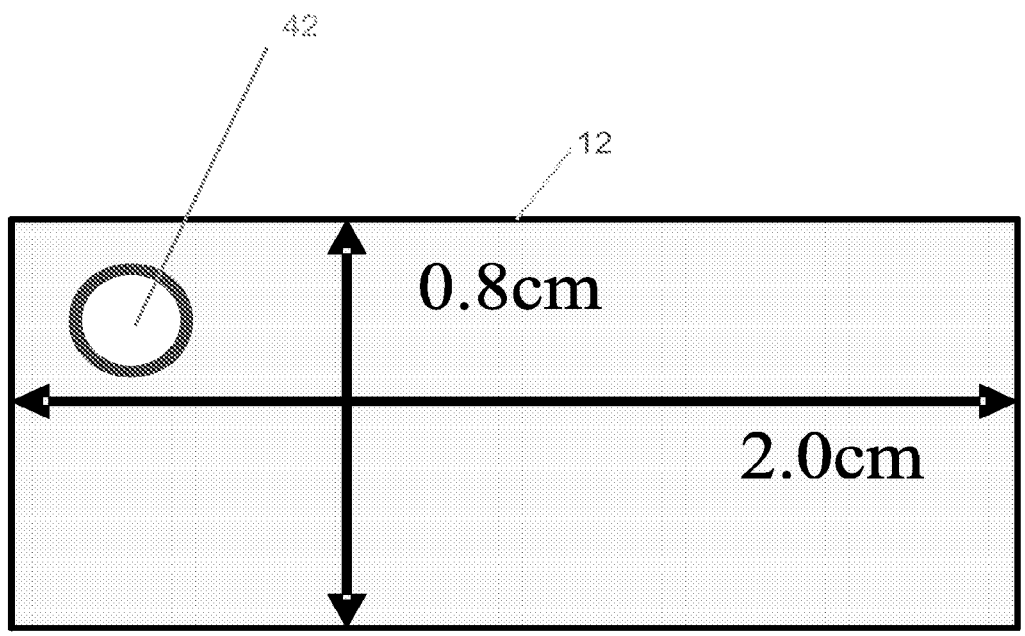
FIG. 20 illustrates a construction in accordance with an exemplary embodiment of the present invention.
Figure 21A:
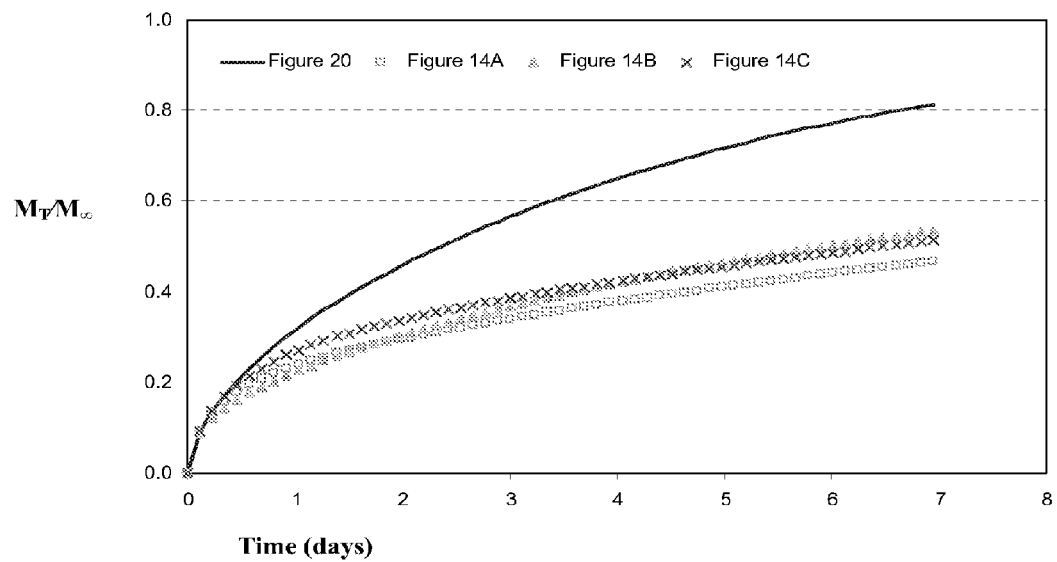
FIGS. 21A-21D are plots depicting elution rates for the constructions in FIGS. 14A-14J compared to the construction in FIG. 20.
Figure 21B:
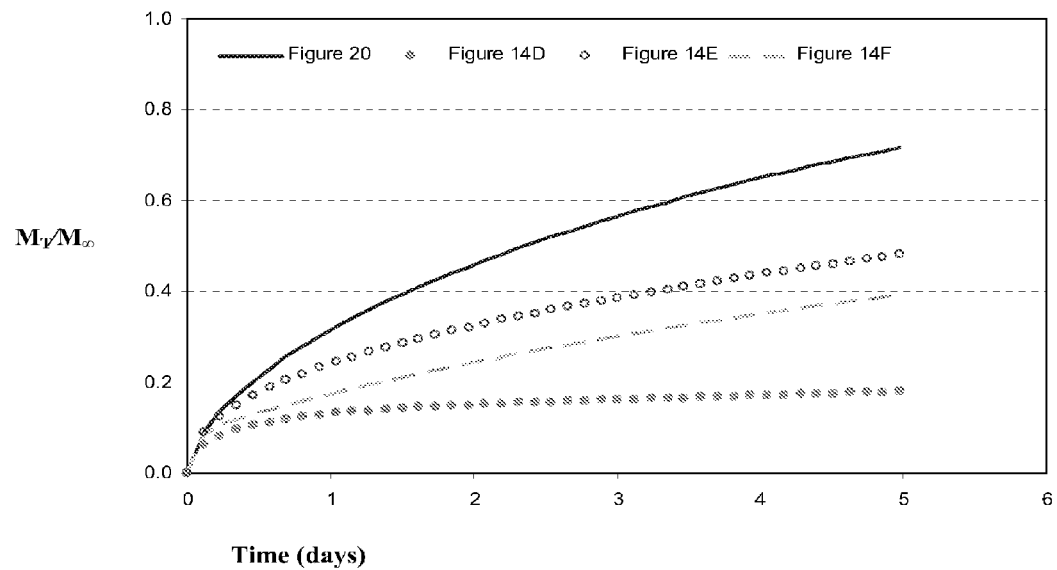
Figure 21C:
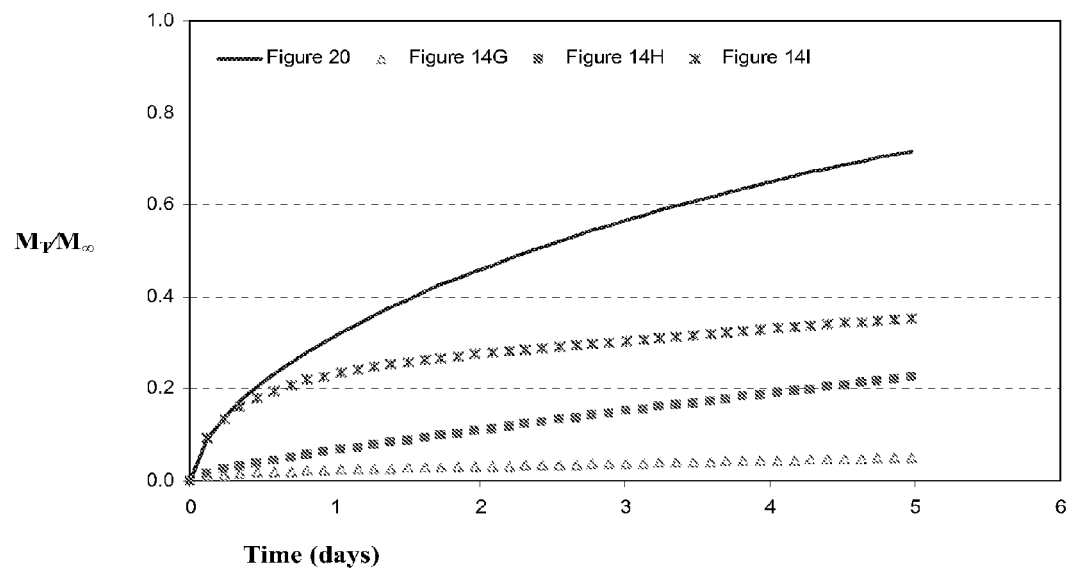
Figure 21D:
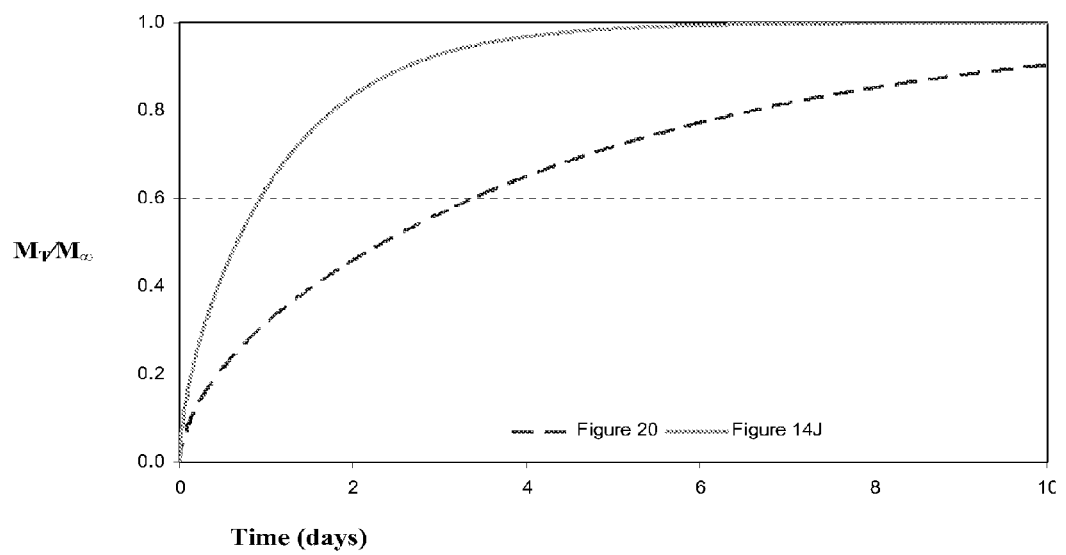
Figure 22I:
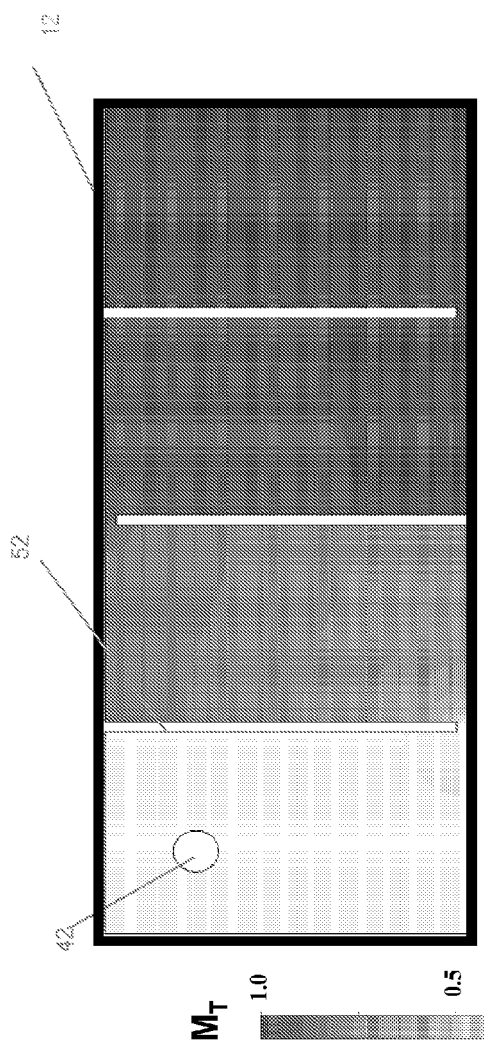
Figure 22J:
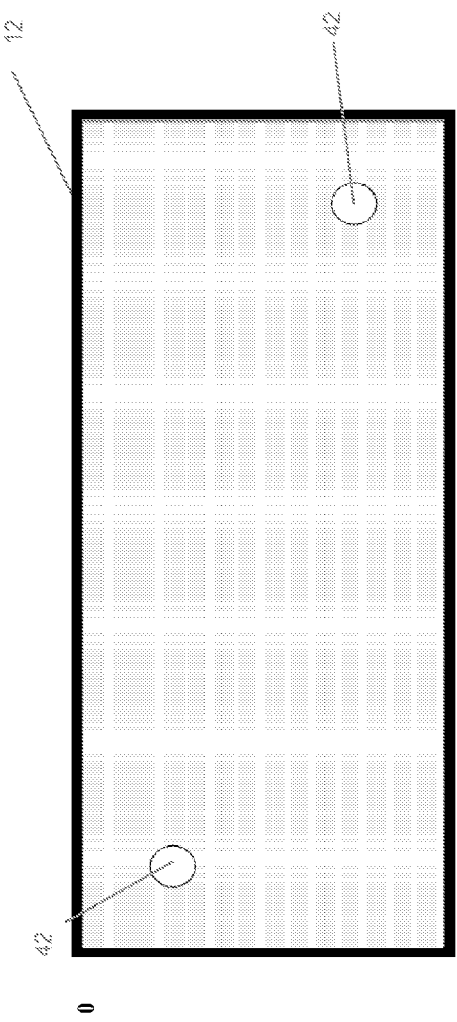
Figure 23A:
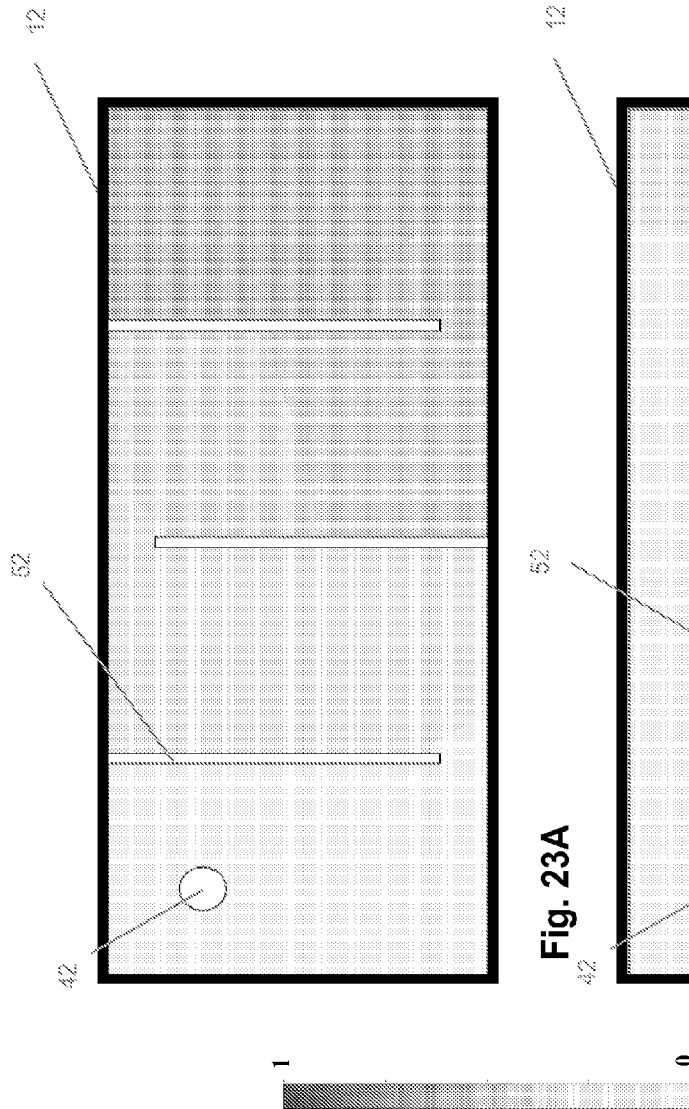
Figure 23B:
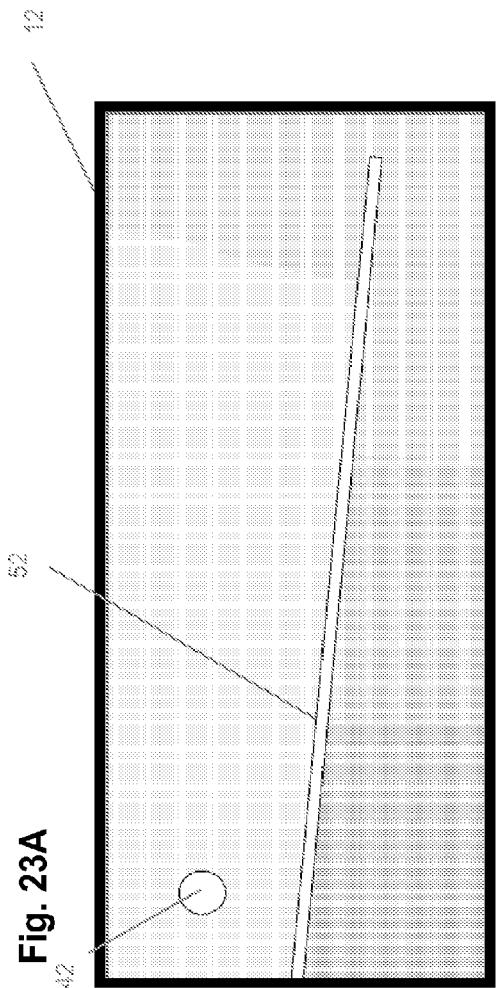
Figures 23G, 23H:
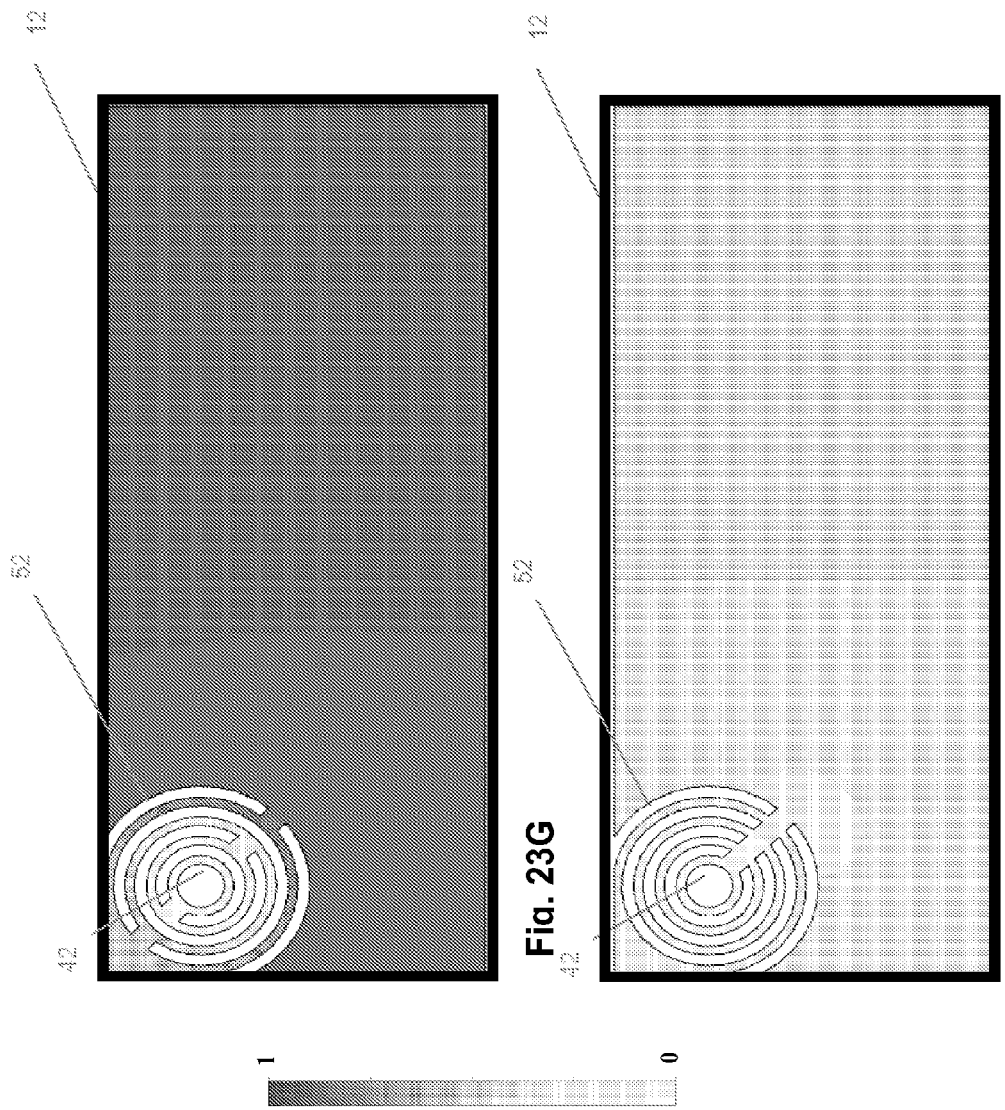

Finally, the validated CFD analysis was used to generate solutions for elution rates across the geometry of the construct in FIG. 20 and the more complex geometries of FIGS. 14A-14J. Note the construct in FIG. 20 is a dimensioned version of that shown in FIGS. 8A and 8B noting that the thickness of the construction in FIG. 20 is modeled in two dimensions (because of the assumption that the thickness of the model is significantly smaller than the x- or y-dimensions, which is well-supported with the validation presented above). Irrespective of the modeled geometry, the boundary conditions, material properties and loads were kept the same.

FIGS. 21A-21D depict percent elution versus days elapsed for the constructions in FIGS. 14A-14J compared to the construction in FIG. 20. FIGS. 22A-22J depict therapeutic agent concentration at T=2.5 days for the constructions in FIGS. 14A-14J. FIGS. 23A-23I depict therapeutic agent concentration at T=20 days for the constructions in FIGS. 14A-14I.

Example 3

Figure 25A:
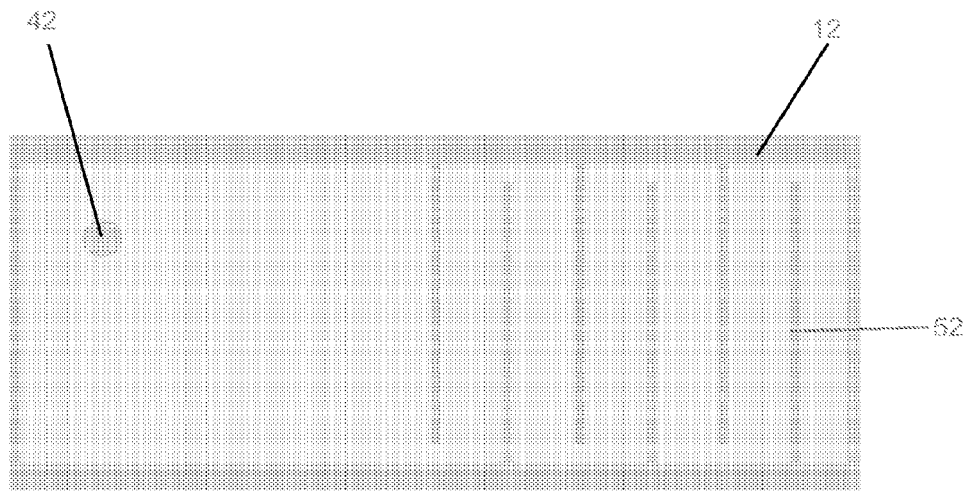
FIG. 25A illustrates an embodiment of the present invention.

In this example, the validated CFD analysis method described above was used to generate solutions for comparative elution rates across the construction geometries shown in FIGS. 17A and 25A. The construction geometries were modeled in two dimensions (because of the assumption that the thickness of the model is significantly smaller than the x- or y-dimensions, which is well-supported with the validation presented) and the models were meshed utilizing SolidWorks 2010 SP3.0 and Ansys 12.1. A triangular (3-node) mesh was selected with an interval size of $4 \times 10^{-4}$ m. Appropriate boundary conditions were applied and material properties were assigned. There was a zero diffusive flux across the walls, so that diffusion only occurred at the outlet. The convective term at the outlet was also neglected. Initially the entire geometry of the constructions in FIGS. 17A and 25A was assumed to be coated with the drug so that the there were no voids, and the concentration of the drug at the outlet was zero. The density, viscosity, and molecular weight for each species were set to 1 and the diffusion coefficient was set to $4 \times 10^{-6}$ cm$^2$/s. Irrespective of the modeled geometry, the material properties and loads were kept the same. The CFD analysis of the construction in FIG. 25A assumed there was no gate affecting elution of the therapeutic agent such as gate (98) in FIG. 17A. For FIG. 17A, the gate (98) was initially assumed to represent a wall with zero diffusive flux. After one day (T=1 day) had elapsed, the second application (the right side of FIG. 17A) of the therapeutic agent was allowed to release as the gate was assumed to have dissolved (i.e., opened).

Figure 25B:
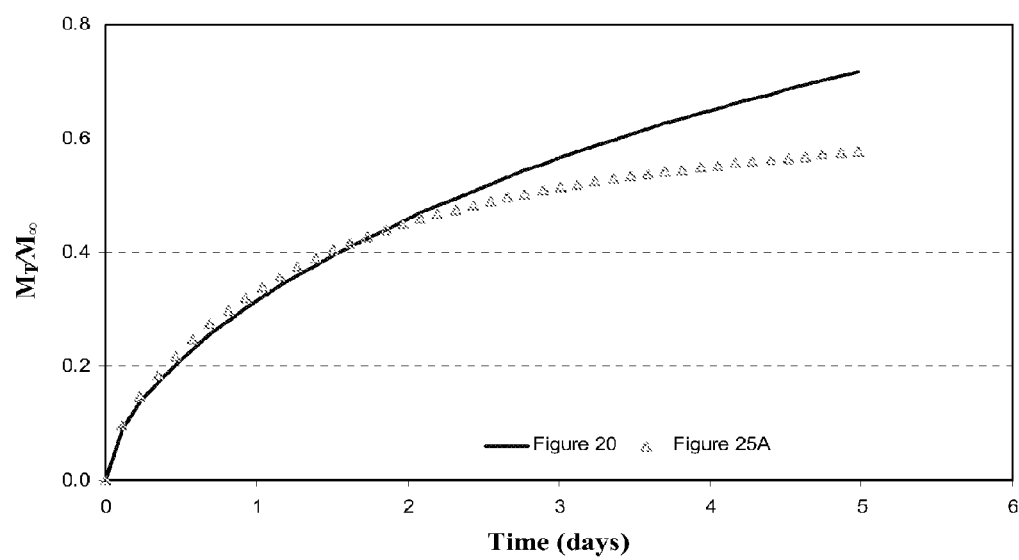
FIG. 25B is a plot comparing elution rates for the constructions in FIG. 20 and in FIG. 25A.

FIG. 25B is a plot depicting percent elution versus days elapsed for the geometry with barriers (52) shown in FIG. 25A as compared to the construction without barriers in FIG. 20. As can be seen, the elution profile for the construction in FIG. 25A is slower then that for the construction shown in FIG. 20 due to the presence and locations of barriers (52).

Figure 26:
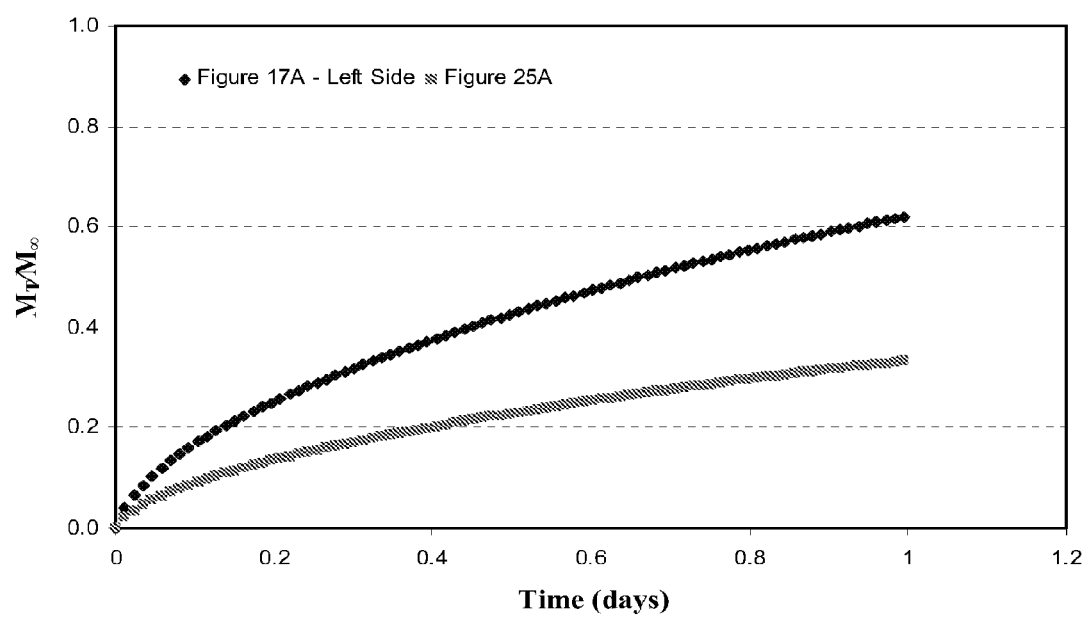
FIG. 26 is a plot depicting elution rates for the left hand side of the construction in FIG. 17A with that in FIG. 25A.

FIG. 26 is a plot depicting comparative elution profiles over one day (T=1.0) between the left hand portion of the constructions shown in FIG. 17A with gate (98) closed and the entire construction shown in FIG. 25A which has no such gate. The initial, shorter diffusion length of FIG. 17A (the higher plot line) is evident as compared to that for the construct in FIG. 25A. Similar to the previously validated studies, when a shorter diffusion length is employed the rate of diffusion is faster. Since FIG. 17A has the gate closed the diffusion length is only half of the surface, whereas FIG. 25A is the entire surface, becoming a much larger diffusion length and thus slower rate of diffusion.

Figure 27B:
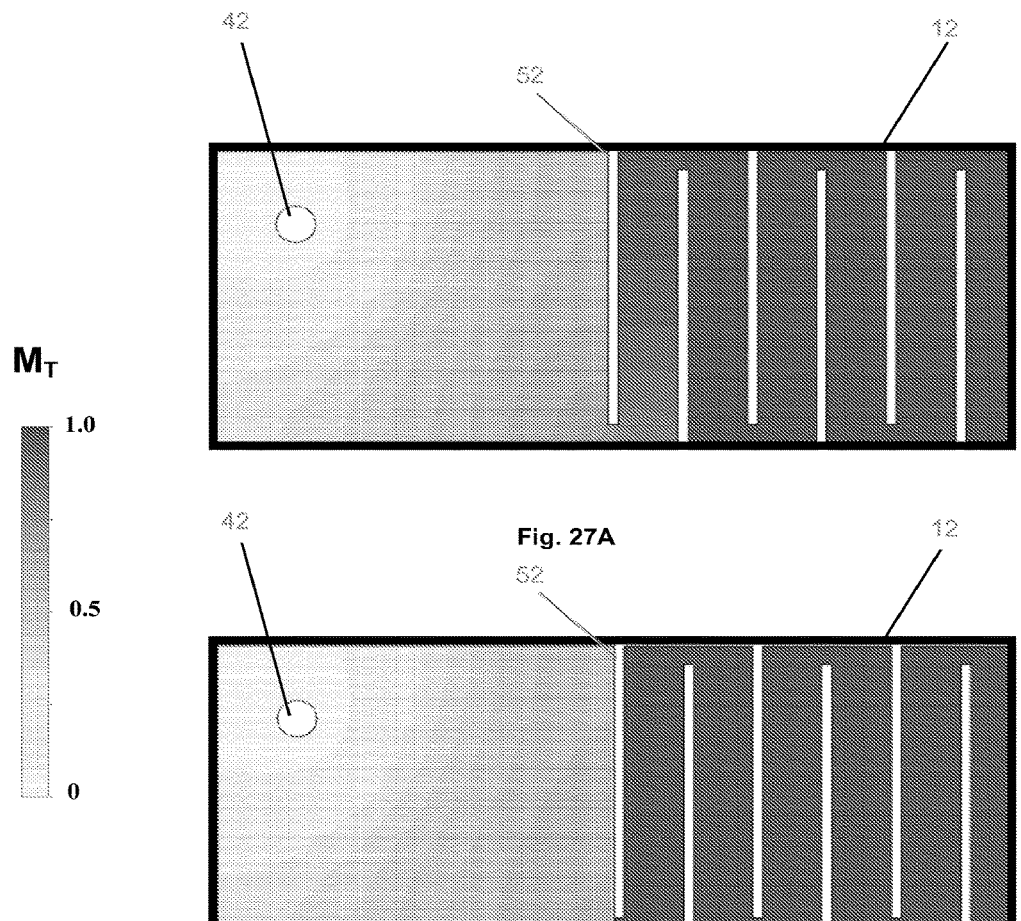

FIGS. 27A and 27B depict therapeutic agent concentrations at T=22.5 hours for constructions shown in FIGS. 25A and 17A, respectively. Referring to FIG. 27A, it is apparent from the shading that the model therapeutic agent has begun to move from the volume on the right hand side of the first barrier (52) (located in the middle of the construction) toward hole 42. Conversely, in FIG. 27B the volume of the model drug to the right of the first barrier (52) is held in place because gate (98) in FIG. 17A has not opened.

Figure 24A:
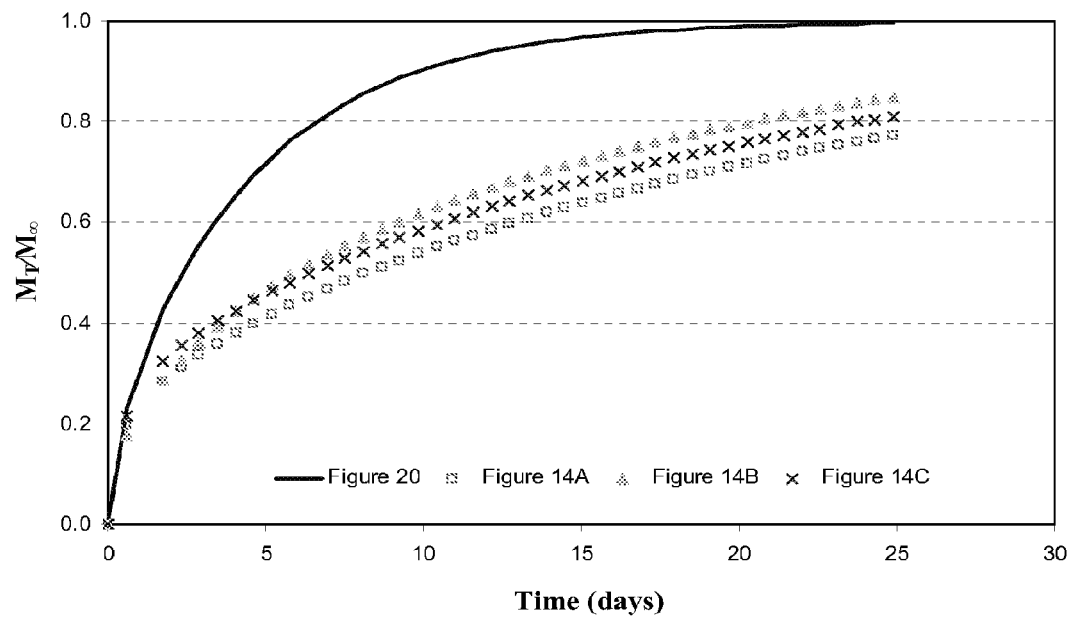
FIGS. 24A-24C are longer term plots depicting elution rates for the constructions in FIGS. 14A-14I compared to the construction in FIG. 20.
Figure 24B:
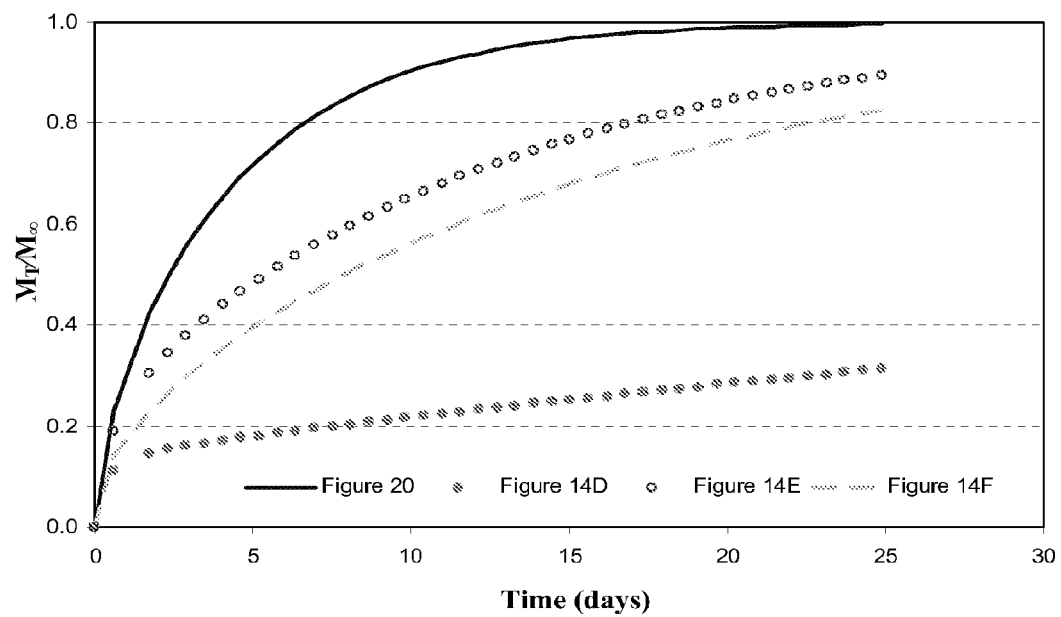
Figure 24C:
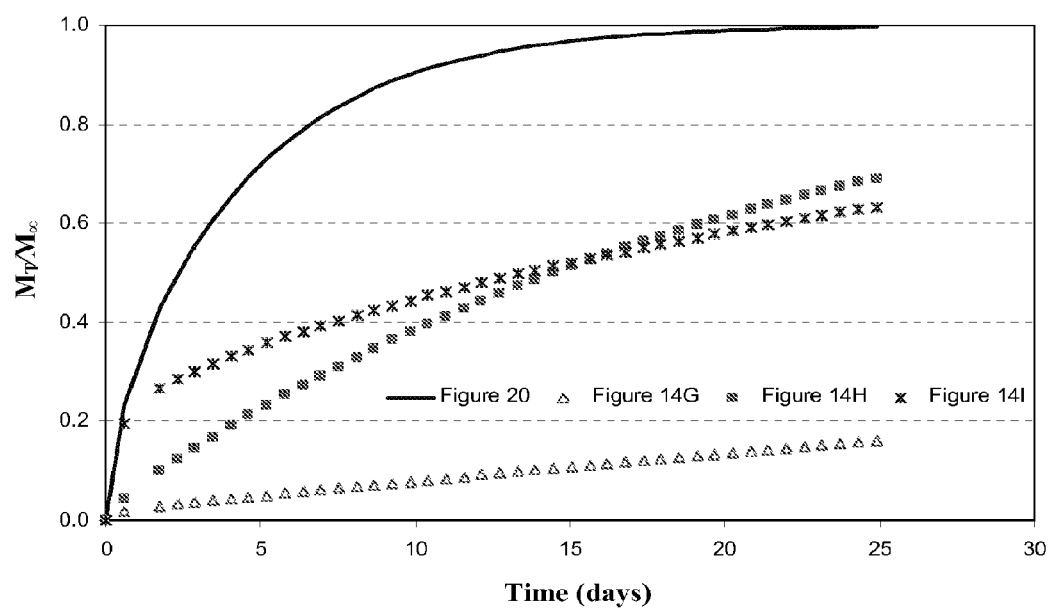

FIGS. 24A-24C depict the fraction of therapeutic agent eluted versus days elapsed for the constructions in FIGS. 14A-14I compared to the construction in FIG. 20. The longer term elution rates shown in FIGS. 24A, 24B and 24C (versus those shown in FIGS. 21A-21C) demonstrate how the rate of diffusion changes with time in the different embodiments. For example referring to FIG. 24A, prior to day 5, the configuration shown in FIG. 14C shows a faster rate of elution, whereas that for the construction in 14B is slower. However, beyond 5 days the rate for the construct in FIG. 14B surpasses that of the construction in FIG. 14C. This is shown again by comparing the elution rates for constructions in FIGS. 14I and 14H prior to day 5, against rates at around day 15 for the same constructs shown in FIG. 24C. In each case this is related to the accessibility of drug in the second (or third or fourth) partition (i.e., those areas between barriers (52)). Put another way, it is the gradual accumulation of diffusion length as each segment of the construct is accessed that causes this effect.

The therapeutic agent closest to the outlet naturally has a shorter diffusion length (and faster rate of diffusion) whereas the drug that is farthest from the outlet has the longest path and slowest rate of diffusion. As the drug on each subsection or partition between barriers (52) diffuses, a concentration gradient is created which initiates diffusion from the next section. As the drug on each subsequent section diffuses, there is an accumulation of effective diffusion length. The points at which the diffusion curves in FIGS. 24A-24C intersect represent the time when the effective diffusion lengths for each respective configurations are equal.

For example, the constructions shown in FIGS. 14A and 14C feature barriers (52) the shape, size, and angles of which are identical and serve to create four reservoirs or partitioned areas (from left to right in the drawings). The only difference between the constructions in FIGS. 14A and 14C is the diffusion path length between opening (42) and the second partition. As shown in FIG. 24A, initially each construct has very similar diffusion rates because the initial path (i.e., from the first partition) is short. However, as shown in FIG. 14C the gap between barrier (52) and side of the impermeable material (12) is closer to the outlet and therefore there is a closer proximity to the second partition, and a second diffusion length. In the construction shown in FIG. 14A diffusion occurs from one direction (bottom towards top) whereas for the construction in FIG. 14C diffusion occurs in two directions (bottom towards top and left to right). After about 7 days of diffusion the effect is evident as the rate of diffusion for FIG. 14C becomes greater than that for FIG. 14A as shown in the plot in FIG. 24A. Once the additional partitions in the constructs in FIGS. 14A and 14C are accessed the overall shorter diffusion length of the construct in FIG. 14C remains clear as the amount diffused from the construct in FIG. 14A is consistently less than the amount diffused from the construct in FIG. 14C for any given point in time.

Similarly, the construct in FIG. 14B initially is drawing from a distance that is equivalent to the length (from left to right in the Figure) of the construct. Consequently, the theory shown in the plots in FIG. 19B applies, where a longer diffusion length equates to a slower elution. However once the accumulated effective diffusion length of the construct in FIG. 14C becomes greater than that of the construct in FIG. 14B, that is when enough partitions are involved in the diffusion process, the amount diffused from the construct in FIG. 14B becomes greater than that diffused from the construct in FIG. 14C.

The invention claimed is:

1. A therapeutic-releasing device comprising:
   a first therapeutic-releasing construction including:
      a first coated film;
      a first therapeutic agent incorporated within the first coated film;
      a first capping layer that substantially covers all of the first coated film and is impermeable to the first therapeutic agent;
      a first opening in the first capping layer;
      a first elution pathway for the first therapeutic agent through the first coated film that exits the first coated film at the first opening, and
   a second therapeutic-releasing construction including:
      a second coated film;
      a second therapeutic agent incorporated within the second coated film;
      a second capping layer that substantially covers all of the second coated film and is impermeable to the second therapeutic agent;
      a second opening in the second capping layer; and
      a second elution pathway for the second therapeutic agent through the second coated film that exits the second coated film at the second opening,
   wherein the first therapeutic-releasing construction is stacked inside the second therapeutic-releasing construction;
   wherein a first portion of the first capping layer is fused together with a second portion of the first capping layer such that the first capping layer extends through the first coated film to form a barrier that is substantially impermeable to the first therapeutic agent and defines the first elution pathway; and
   wherein the first portion of the first capping layer is on a first side of the first coated film and the second portion of the first capping layer is on second side of the first coated film that is opposite to the first side.

2. The therapeutic-releasing device of claim 1, wherein the first opening and the second opening expose the first coated film and the second coated film, respectively, to an external environment.

3. The therapeutic-releasing device of claim 2, wherein the first opening is aligned with the second opening.

4. The therapeutic-releasing device of claim 2, wherein the first opening is offset from the second opening.

5. The therapeutic-releasing device of claim 1, wherein the first therapeutic agent has a first potency and the second therapeutic agent has a second potency.

6. The therapeutic-releasing device of claim 1, wherein the first therapeutic agent is the same as the second therapeutic agent.

7. The therapeutic-releasing device of claim 1, the first coated film is expanded polytetrafluoroethylene impregnated with a copolymer into which has been admixed the first therapeutic agent, and the second coated film is expanded polytetrafluoroethylene impregnated with the copolymer into which has been admixed the second therapeutic agent.

8. The therapeutic-releasing device of claim 1, wherein the first capping layer is a silicone composition and the second capping layer is the silicone composition.

9. The therapeutic-releasing device of claim 1, wherein the first therapeutic-releasing construction is in a form of a cylinder and the second therapeutic-releasing construction is in a form of a cylinder.

10. The therapeutic-releasing device of claim 9, wherein the first therapeutic-releasing construction is enclosed on both ends of the cylinder and the second therapeutic-releasing construction is enclosed on both ends of the cylinder.

11. The therapeutic-releasing device of claim 1, wherein the first elution pathway is configured such that the first therapeutic agent exits the first coated film after a first predetermined period of time, and wherein the second elution pathway is configured such that the second therapeutic agent exits the second coated film after a second predetermined period of time that is longer than the first predetermined period of time.

12. The therapeutic-releasing device of claim 1, wherein the first therapeutic-releasing construction and the second therapeutic-releasing construction are in a form of a cylinder; the second therapeutic-releasing construction encases a portion of the first therapeutic-releasing construction; and the first opening and the second opening expose the first coated film and the second coated film, respectively, to an external environment.

13. A therapeutic-releasing device comprising:
a plurality of therapeutic-releasing constructions stacked inside one another, wherein each of the therapeutic-releasing constructions includes:
a coated film;
a therapeutic agent incorporated within the coated film;
a capping layer that substantially covers all of the coated film and is impermeable to the therapeutic agent;
an opening in the capping layer; and
an elution pathway for the therapeutic agent through the coated film that exits the coated film at the opening,
wherein the coated film is a polymeric material comprising one or more polymeric barriers that are substantially impermeable to the therapeutic agent and define the elution pathway, and
wherein the one or more polymeric barriers have a length such that the one or more polymeric barriers extend from a first edge of the coated film towards a second edge of the coated film, and end a predetermined distance away from the second edge.

14. The therapeutic-releasing device of claim 13, wherein the coated film is a polymeric material comprising one or more polymeric barriers that are substantially impermeable to the therapeutic agent and define the elution pathway.

15. The therapeutic-releasing device of claim 14, the coated film is expanded polytetrafluoroethylene impregnated with a copolymer into which has been admixed the therapeutic agent.

16. The therapeutic-releasing device of claim 15, wherein each of the therapeutic-releasing constructions is in a form of a cylinder.

17. A therapeutic-releasing device comprising:
a plurality of therapeutic-releasing constructions stacked inside one another, wherein each of the therapeutic-releasing constructions includes:
a coated film;
a therapeutic agent incorporated within the coated film;
a capping layer that substantially covers an exterior surface of the coated film and is impermeable to the therapeutic agent;
a substrate that completely covers an interior surface of the coated film and is impermeable to the therapeutic agent;
an elution pathway for the therapeutic agent through the coated film that exits from portions of the coated film not covered by the capping layer; and
one or more biocompatible polymeric barriers disposed within the coated film that are substantially impermeable to the therapeutic agent and define the elution pathway, wherein the one or more biocompatible polymeric barriers have a height such that each of the one or more biocompatible polymeric barriers extends a full vertical distance between the capping layer and the substrate.

* * * * *